US012628247B2

(12) United States Patent
Sur

(10) Patent No.: US 12,628,247 B2
(45) Date of Patent: May 12, 2026

(54) SUSCEPTOR ARRANGEMENT FOR INDUCTION-HEATED AEROSOL DELIVERY DEVICE

(71) Applicant: RAI STRATEGIC HOLDINGS, INC., Winston-Salem, NC (US)

(72) Inventor: Rajesh Sur, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 1963 days.

(21) Appl. No.: 16/260,712

(22) Filed: Jan. 29, 2019

(65) Prior Publication Data
US 2020/0237018 A1     Jul. 30, 2020

(51) Int. Cl.
*H05B 6/36*       (2006.01)
*A61M 11/04*      (2006.01)
*H05B 6/10*       (2006.01)

(52) U.S. Cl.
CPC .............. *H05B 6/36* (2013.01); *H05B 6/105* (2013.01); *A61M 11/042* (2014.02)

(58) Field of Classification Search
CPC ........ H05B 6/36; H05B 6/105; H05B 3/0014; H05B 3/44; H05B 6/108; A61M 11/042; A24F 40/20; A24F 40/465; A24F 40/42; A24F 40/10; A24F 40/485; A24F 7/00; A24F 40/00; A24F 40/50; A24F 40/60; A24F 47/00; A24B 15/167; A24D 1/002; A24D 1/20; B65D 85/804; B65D 43/02
USPC ........ 131/329, 194; 219/630, 628, 631, 629, 219/635, 672, 670, 618, 634, 674, 660, 219/667, 600, 535, 654, 643, 553, 494,
(Continued)

(56) References Cited

U.S. PATENT DOCUMENTS 2,057,353 A     10/1936   Whittemore, Jr.
2,104,266 A      1/1938   McCormick
(Continued)

FOREIGN PATENT DOCUMENTS

CN        1541577 A     11/2004
CN        2719043 Y      8/2005
(Continued)

OTHER PUBLICATIONS

CN 104188108 (Year: 2014).*
(Continued)

*Primary Examiner* — Vy T Nguyen
(74) *Attorney, Agent, or Firm* — Womble Bond Dickinson (US) LLP

(57)          ABSTRACT

An aerosol delivery device and an aerosol source member for use with an aerosol delivery device are provided. In various implementations, the aerosol source member comprises a substrate portion that includes a plurality of spaced susceptor bands. In one implementation, each susceptor band comprises a plurality of susceptor coils that are radially spaced around the longitudinal axis of the substrate portion, wherein each of the susceptor coils defines a longitudinal axis thereof, and wherein the longitudinal axis of each of the plurality of susceptor coils is substantially parallel to the longitudinal axis of the substrate portion. In another implementation, each susceptor band extends through the center of the substrate portion and across a diameter thereof, and wherein each susceptor band comprises a plurality of spaced susceptor particles.

9 Claims, 10 Drawing Sheets

(58) Field of Classification Search
USPC ....... 219/647, 601, 632, 482, 676, 539, 649,
219/669, 671, 677, 201, 633, 503, 552,
219/662, 528, 540, 624, 651, 652, 675,
219/687, 209, 490, 549, 621, 260, 401,
219/492, 50, 541, 543, 607, 616, 619,
219/627, 638, 639, 650, 673, 688, 772,
219/121.39, 263, 269, 483, 497, 530, 533,
219/546, 622, 656, 116, 121.36, 121.43,
219/121.48, 121.54, 121.6, 121.85, 129,
219/200, 202, 205, 208, 214, 220, 240,
219/241, 262, 267, 385, 388, 428, 436,
219/477, 480, 486, 505, 507, 511, 534,
219/536, 538, 544, 548, 602, 603, 620,
219/636, 637, 644, 655, 659, 66, 661,
219/663, 665, 666, 668, 725, 731, 759,
219/777, 778, 779, 121.69, 203, 227, 268,
219/386, 438, 439, 474, 501, 508, 510,
219/520, 521, 525, 537, 542, 550, 608,
219/679
See application file for complete search history.

(56) References Cited

U.S. PATENT DOCUMENTS

| | | |
|---|---|---|
| 3,200,819 A | 8/1965 | Gilbert |
| 4,922,901 A | 5/1990 | Brooks et al. |
| 5,060,671 A | 10/1991 | Counts et al. |
| 5,093,894 A | 3/1992 | Deevi et al. |
| 5,261,424 A | 11/1993 | Sprinkel, Jr. |
| 5,345,951 A | 9/1994 | Serrano et al. |
| 5,388,574 A | 2/1995 | Ingebrethsen et al. |
| 5,530,225 A | 6/1996 | Hajaligol |
| 5,613,505 A * | 3/1997 | Campbell ............... A24F 40/53 |
| | | 131/194 |
| 5,687,746 A | 11/1997 | Rose et al. |
| 5,726,421 A | 3/1998 | Fleischhauer et al. |
| 5,865,185 A | 2/1999 | Collins et al. |
| 5,894,841 A | 4/1999 | Voges |
| 6,125,853 A | 10/2000 | Susa et al. |
| 6,155,268 A | 12/2000 | Takeuchi |
| 7,117,867 B2 | 10/2006 | Cox et al. |
| 7,832,410 B2 | 11/2010 | Hon |
| 8,314,591 B2 | 11/2012 | Terry et al. |
| 8,365,742 B2 | 2/2013 | Hon |
| 8,499,766 B1 | 8/2013 | Newton |
| 2002/0078951 A1 | 6/2002 | Nichols et al. |
| 2005/0016550 A1 | 1/2005 | Katase |
| 2006/0196518 A1 | 9/2006 | Hon |
| 2007/0235046 A1 * | 10/2007 | Gedevanishvili ...... A24D 3/046 |
| | | 131/201 |
| 2008/0092912 A1 | 4/2008 | Robinson et al. |
| 2009/0095311 A1 | 4/2009 | Hon |
| 2009/0126745 A1 | 5/2009 | Hon |
| 2009/0188490 A1 | 7/2009 | Hon |
| 2009/0272379 A1 | 11/2009 | Thorens et al. |
| 2011/0094523 A1 | 4/2011 | Thorens et al. |
| 2011/0126848 A1 | 6/2011 | Zuber et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0290248 A1 | 12/2011 | Schennum |
| 2012/0111347 A1 | 5/2012 | Hon |
| 2012/0260927 A1 | 10/2012 | Liu |
| 2012/0279512 A1 | 11/2012 | Hon |
| 2013/0037041 A1 | 2/2013 | Worm et al. |
| 2013/0056013 A1 | 3/2013 | Terry et al. |
| 2013/0306084 A1 | 11/2013 | Flick |
| 2014/0000638 A1 | 1/2014 | Sebastian et al. |
| 2014/0060554 A1 | 3/2014 | Collett et al. |
| 2014/0060555 A1 | 3/2014 | Chang et al. |

| | | |
|---|---|---|
| 2014/0096781 A1 | 4/2014 | Sears et al. |
| 2014/0096782 A1 | 4/2014 | Ampolini et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2015/0223292 A1 | 8/2015 | Duffield et al. |
| 2015/0245669 A1 | 9/2015 | Cadieux et al. |
| 2016/0295921 A1 * | 10/2016 | Mironov ............... A24F 40/465 |
| 2017/0055575 A1 | 3/2017 | Wilke et al. |
| 2017/0055582 A1 | 3/2017 | Blandino et al. |
| 2017/0055583 A1 | 3/2017 | Blandino et al. |
| 2017/0055584 A1 | 3/2017 | Blandino et al. |
| 2017/0064996 A1 | 3/2017 | Mironov |
| 2017/0071250 A1 | 3/2017 | Mironov et al. |
| 2017/0079325 A1 | 3/2017 | Mironov |
| 2017/0079326 A1 | 3/2017 | Mironov |
| 2018/0027884 A1 * | 2/2018 | Zuber ............... A61M 15/0036 |
| 2018/0352862 A1 | 12/2018 | Mironov et al. |
| 2019/0053535 A1 * | 2/2019 | Apetrei Birza ........... A24F 7/00 |

FOREIGN PATENT DOCUMENTS

| | | |
|---|---|---|
| CN | 201379072 Y | 1/2010 |
| CN | 105263346 A | 1/2016 |
| CN | 107920597 A | 4/2018 |
| CN | 108135266 A | 6/2018 |
| CN | 108135276 A | 6/2018 |
| CN | 207492080 U | 6/2018 |
| CN | 108347999 A | 7/2018 |
| CN | 108367129 A | 8/2018 |
| EP | 0 295 122 A2 | 12/1988 |
| EP | 0 845 220 A1 | 6/1998 |
| EP | 1 618 803 A1 | 1/2006 |
| GB | 2469850 A | 11/2010 |
| KR | 10-2009-0080005 A | 7/2009 |
| RU | 2677111 C2 | 1/2019 |
| WO | 95/27411 | 10/1995 |
| WO | 2003/034847 A1 | 5/2003 |
| WO | 2004/080216 A1 | 9/2004 |
| WO | 2005/099494 A1 | 10/2005 |
| WO | 2007/131449 A1 | 11/2007 |
| WO | 2011/139730 A1 | 11/2011 |
| WO | 2014/048745 | 4/2014 |
| WO | 2015/177046 A1 | 11/2015 |
| WO | 2015/177252 A1 | 11/2015 |
| WO | 2015/177263 | 11/2015 |
| WO | 2015/177264 A1 | 11/2015 |
| WO | 2015/198015 | 12/2015 |
| WO | 2017/036957 A1 | 3/2017 |
| WO | 2017/036959 | 3/2017 |
| WO | 2017/068096 A1 | 4/2017 |
| WO | 2017/068098 A1 | 4/2017 |
| WO | 2017/068100 A1 | 4/2017 |
| WO | 2017068093 A | 4/2017 |
| WO | 2018/002084 A1 | 1/2018 |
| WO | WO-2018041924 A1 * | 3/2018 ............. A24B 15/12 |
| WO | WO-2018178216 A1 * | 10/2018 ........... A24B 15/167 |
| WO | 2018/206616 A1 | 11/2018 |
| WO | 2018/211084 A1 | 11/2018 |
| WO | 2020/079130 A1 | 4/2020 |

OTHER PUBLICATIONS

Partial International Search Report from corresponding International Application No. PCT/IB2020/050619, mailed Jan. 27, 2020.
International Search Report from the corresponding International Application No. PCT/IB2020/050619, dated Jul. 30, 2020.

* cited by examiner

SUSCEPTOR ARRANGEMENT FOR INDUCTION-HEATED AEROSOL DELIVERY DEVICE

TECHNOLOGICAL FIELD

The present disclosure relates to aerosol source members, aerosol delivery devices, and uses thereof for yielding tobacco components or other materials in inhalable form. More particularly, the present disclosure relates to aerosol source members and aerosol delivery devices and systems, such as smoking articles, that utilize electrically-generated heat to heat tobacco or a tobacco derived material, preferably without significant combustion, in order to provide an inhalable substance in the form of an aerosol for human consumption.

BACKGROUND

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference in their entireties. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference in its entirety. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No.

6,772,756 to Shayan; U.S. Pat. Pub. No. 2009/0095311 to Hon; U.S. Pat. Pub. Nos. 2006/0196518, 2009/0126745, and 2009/0188490 to Hon; U.S. Pat. Pub. No. 2009/0272379 to Thorens et al.; U.S. Pat. Pub. Nos. 2009/0260641 and 2009/0260642 to Monsees et al.; U.S. Pat. Pub. Nos. 2008/0149118 and 2010/0024834 to Oglesby et al.; U.S. Pat. Pub. No. 2010/0307518 to Wang; and WO 2010/091593 to Hon, which are incorporated herein by reference in their entireties.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUIFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™ HENDU™ JET™, MAXXQ™ PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd; IQOS™ by Philip Morris International; and GLO™ by British American Tobacco. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™.

Articles that produce the taste and sensation of smoking by electrically heating tobacco or tobacco derived materials have suffered from inconsistent performance characteristics. Accordingly, it is desirable to provide a smoking article that can provide the sensations of cigarette, cigar, or pipe smoking, without substantial combustion, and that does so with advantageous performance characteristics.

BRIEF SUMMARY

In various implementations, the present disclosure provides an aerosol delivery device and an aerosol source member for use with an induction heated aerosol delivery device having a resonant transmitter. In one implementation, the aerosol source member comprises a substrate portion that defines a longitudinal axis and includes a plurality of spaced susceptor bands. Each susceptor band may comprise a plurality of susceptor coils that are radially spaced around the longitudinal axis of the substrate portion, each of the susceptor coils may define a longitudinal axis, and the longitudinal axis of each of the plurality of susceptor coils may be substantially parallel to the longitudinal axis of the substrate portion. In some implementations, the plurality of susceptor bands may be substantially evenly spaced. In some implementations, the plurality of susceptor coils in each susceptor band may be substantially evenly spaced. Some implementations may further comprise a cover layer disposed around the substrate portion. In some implementations, the cover layer may comprise a foil sublayer and a paper sublayer disposed around the foil sublayer. In some implementations, the plurality of susceptor coils may comprise cobalt, iron, nickel, and combinations thereof. In some implementations, the substrate portion may comprise an extruded tobacco material. In some implementations, the substrate portion may comprise a reconstituted tobacco sheet material. In some implementations, the substrate portion may comprise at least one of tobacco beads and tobacco powder. In some implementations, the aerosol source member may have a substantially cylindrical shape.

In another implementation, the aerosol source member comprises a substrate portion that includes a plurality of spaced susceptor bands. Each susceptor band may extend through the center of the substrate portion and across a diameter thereof, and each susceptor band may comprise a plurality of spaced susceptor particles. In some implementations, the plurality of susceptor particles may be substantially aligned within each susceptor band. In some implementations, the plurality of susceptor bands may be substantially evenly spaced. In some implementations, the plurality of susceptor particles may be substantially evenly spaced within each susceptor band. Some implementations may further comprise a cover layer disposed around the substrate portion. In some implementations, the cover layer may comprise a foil sublayer and a paper sublayer disposed around the foil sublayer. In some implementations, the plurality of susceptor particles may have a shape selected from a flake-like shape, a spherical shape, a hexagonal shape, a cubic shape, and an irregular shape. In some implementations, the plurality of susceptor particles may comprise a material selected from a cobalt material, an iron material, a nickel material, a zinc material, a manganese material, a stainless steel material, a ceramic material, a silicon carbide material, a carbon material, and combinations thereof. In some implementations, the substrate portion may comprise an extruded tobacco material. In some implementations, the substrate portion may comprise a reconstituted tobacco sheet material. In some implementations, the substrate portion may comprise at least one of tobacco beads and tobacco powder. In some implementations, the aerosol source member may have a substantially cylindrical shape.

In another implementation, the aerosol source member comprises a substrate portion that comprises a core portion, a surrounding portion disposed around the core portion, and a cover layer disposed around the surrounding portion. The core portion may include a plurality of susceptor particles substantially evenly distributed therein and having a first distribution density, the surrounding layer may include a plurality of susceptor particles substantially evenly distributed therein and having a second distribution density, and the first distribution density may be greater than the second distribution density. In some implementations, the core portion and the surrounding portion may comprise the same substrate material having different susceptor particle distribution densities. In some implementations, the core portion and the surrounding portion may comprise separate substrate layers having different susceptor particle distribution densities. In some implementations, the cover layer may comprise a foil sublayer and a paper sublayer disposed around the foil sublayer. In some implementations, at least one susceptor particle of the plurality of susceptor particles may have a shape selected from a flake-like shape, a spherical shape, a hexagonal shape, a cubic shape, and an irregular shape. In some implementations, at least one susceptor particle of the plurality of susceptor particles may comprise a material selected from a cobalt material, an iron material, a nickel material, a zinc material, a manganese material, a stainless steel material, a ceramic material, a silicon carbide material, a carbon material, and combinations thereof. In some implementations, the substrate portion may comprise an extruded tobacco material. In some implementations, the substrate portion may comprise a reconstituted tobacco sheet material. In some implementations, the substrate portion may comprise at least one of tobacco beads and tobacco powder. In some implementations, the aerosol source member may have a cylindrical shape.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
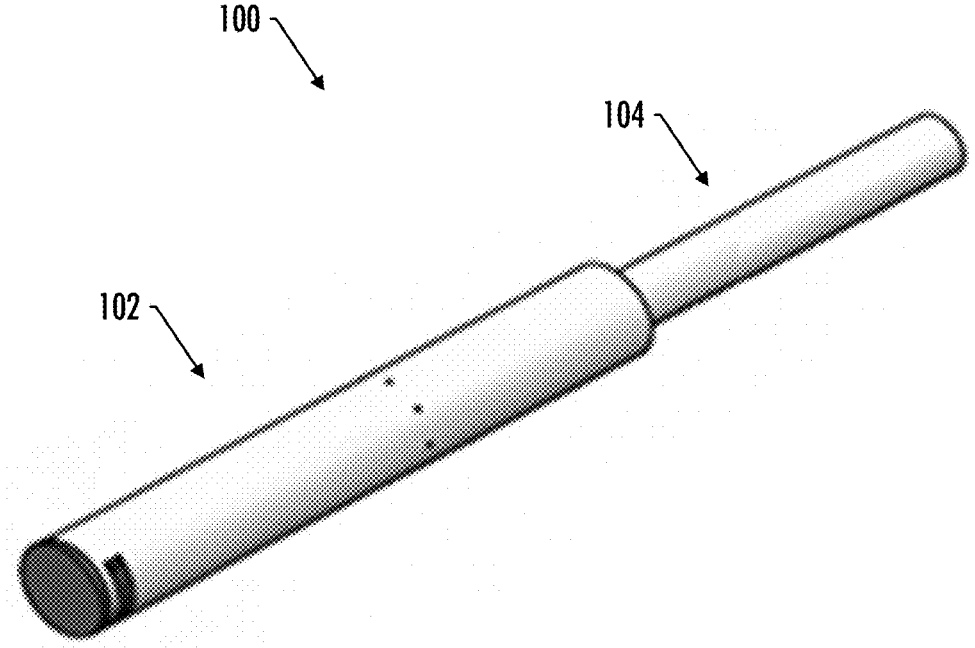
FIG. 1 illustrates a perspective schematic view of an aerosol delivery device comprising a control body and an aerosol source member, wherein the aerosol source member and the control body are coupled to one another, according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Aerosol delivery devices according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called "e-cigarettes" or "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure may also be characterized as being vapor-producing articles or medicament delivery articles. Thus, such articles or devices may be adapted so as to provide one or more substances (e.g., flavors and/or pharmaceutical or nutraceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some implementations, the terms "vapor" and "aerosol" may be interchangeable. Thus, for simplicity, the terms "vapor" and "aerosol" as used to describe aspects of the disclosure are understood to be interchangeable unless stated otherwise.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In another example, an aerosol delivery device may be substantially rectangular or have a substantially rectangular cuboid shape (e.g., similar to a USB flash drive). In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing cartridge containing aerosol precursor material, flavorant, etc.). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices.

As will be discussed in more detail below, aerosol delivery devices of the present disclosure comprise some combination of a power source (e.g., an electrical power source), at least one control component (e.g., means for actuating, controlling, regulating and ceasing power for heat generation, such as by controlling electrical current flow from the power source to other components of the article—e.g., a microprocessor, individually or as part of a microcontroller), a heater or heat generation member (e.g., an electrical resistance heating element or other component and/or an inductive coil or other associated components and/or one or more radiant heating elements), and an aerosol source member that includes or comprises a substrate portion capable of yielding an aerosol upon application of sufficient heat. In some implementations, the aerosol source member may include a mouth end or tip configured to allow drawing upon the aerosol delivery device for aerosol inhalation (e.g., a defined airflow path through the article such that aerosol generated can be withdrawn therefrom upon draw). In other implementations, a control body may include a mouthpiece configured to allow drawing upon for aerosol inhalation.

Alignment of the components within the aerosol delivery device of the present disclosure can vary. In specific implementations, the aerosol source member or substrate portion of the aerosol source member may be positioned proximate a heating member so as to maximize aerosol delivery to the user. Other configurations, however, are not excluded. Generally, the heating member may be positioned sufficiently near the aerosol source member or substrate portion of the aerosol source member so that heat from the heating member can volatilize the aerosol source member or substrate portion of the aerosol source member (as well as, in some implementations, one or more flavorants, medicaments, or the like that may likewise be provided for delivery to a user) and form an aerosol for delivery to the user. When the heating member heats the aerosol source member or substrate portion of the aerosol source member, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device of various implementations may incorporate a power source (e.g., a battery or other electrical power source) to provide current flow sufficient to provide various functionalities to the aerosol delivery device, such as powering of a heating member, powering of an induction coil, powering of control systems, powering of indicators, and the like. The power source can take on various implementations. Preferably, the power source is able to deliver sufficient power to rapidly activate the heating source to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

As noted, aerosol delivery devices may be configured to heat an aerosol source member or a substrate portion of an aerosol source member to produce an aerosol. In some implementations, the aerosol delivery devices may comprise heat-not-burn devices, configured to heat an extruded structure and/or substrate, a substrate material associated with an aerosol precursor composition, tobacco and/or a tobacco-derived material (i.e., a material that is found naturally in tobacco that is isolated directly from the tobacco or synthetically prepared) in a solid or liquid form (e.g., beads, shreds, a wrap, a fibrous sheet or paper), or the like. Such aerosol delivery devices may include so-called electronic cigarettes.

Regardless of the type of substrate material heated, some aerosol delivery devices may include a heating member configured to heat the aerosol source member or substrate portion of the aerosol source member. In some devices, the heating member may comprise a resistive heating member. Resistive heating members may be configured to produce heat when an electrical current is directed therethrough. Such heating members often comprise a metal material and are configured to produce heat as a result of the electrical resistance associated with passing an electrical current therethrough. Such resistive heating members may be positioned in proximity to the aerosol source member or substrate portion of the aerosol source member. Alternatively, the heating member may be positioned in contact with a solid or semi-solid aerosol precursor composition. Such configurations may heat the aerosol source member or substrate portion of the aerosol source member to produce an aerosol. Representative types of solid and semi-solid aerosol precursor compositions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. patnet application Ser. No. 14/755, 205 to Nordskog et al., filed Jun. 30, 2015, all of which are incorporated by reference herein in their entireties.

In the depicted implementations, an inductive heating arrangement is used. In various implementations, the inductive heating arrangement may comprise a resonant transmitter and a resonant receiver (e.g., one or more susceptors, or a plurality of susceptor particles). In such a manner, operation of the aerosol delivery device may require directing alternating current to the resonant transmitter to produce an oscillating magnetic field in order to induce eddy currents in a resonant receiver. In various implementations, the resonant receiver may be part of the aerosol source member or substrate portion of the aerosol source member and/or may be disposed proximate an aerosol source member or substrate portion of an aerosol source member. This alternating current causes the resonant receiver to generate heat and thereby creates an aerosol from the aerosol source member. Some examples of various inductive heating methods and configurations are described in U.S. patent application Ser. No. 15/799,365, filed on Oct. 31, 2017, titled Induction Heated Aerosol Delivery Device, and U.S. patent application Ser. No. 15/836,086, filed on Dec. 8, 2017, titled Quasi Resonant Flyback Converter For An Induction Based Aerosol Delivery Device, each of which is incorporated by reference herein in its entirety. Further examples of various induction-based control components and associated circuits are described in U.S. patent application Ser. No. 15/352,153, filed on Nov. 15, 2016, titled Induction-Based Aerosol Delivery Device, and U.S. Pat. App. Pub. No. 2017/0202266 to Sur et al., each of which is incorporated herein by reference in its entirety. It should be noted that although the depicted implementations describe a single resonant transmitter, in other implementations, there may be multiple independent resonant transmitters, such as, for example, implementations having segmented inductive heating arrangements.

Figure 2:
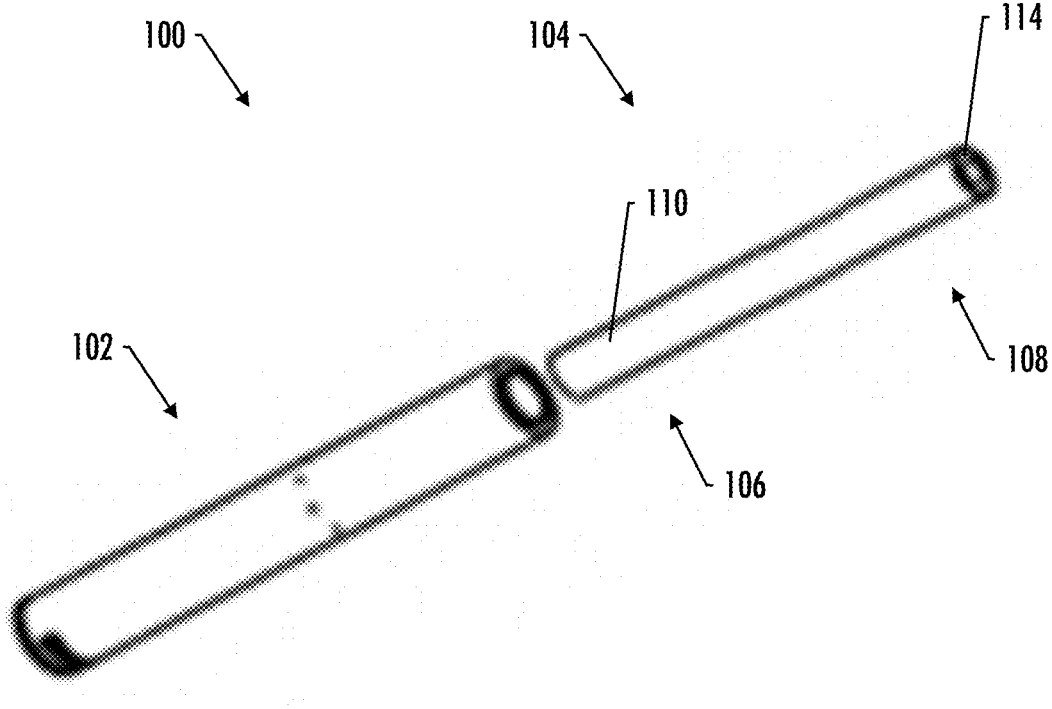
FIG. 2 illustrates a perspective schematic view of the aerosol delivery device of FIG. 1 wherein the aerosol source member and the control body are decoupled from one another, according to an example implementation of the present disclosure.

FIG. 1 illustrates an aerosol delivery device 100 according to an example implementation of the present disclosure. The aerosol delivery device 100 may include a control body 102 and an aerosol source member 104. In various implementations, the aerosol source member 104 and the control body 102 can be permanently or detachably aligned in a functioning relationship. In this regard, FIG. 1 illustrates the aerosol delivery device 100 in a coupled configuration, whereas FIG. 2 illustrates the aerosol delivery device 100 in a decoupled configuration. Various mechanisms may connect the aerosol source member 104 to the control body 102 to result in a threaded engagement, a press-fit engagement, an interference fit, a sliding fit, a magnetic engagement, or the like. In various implementations, the control body 102 of the aerosol delivery device 100 may be substantially rod-like, substantially tubular shaped, substantially rectangular or rectangular cuboidal shaped (e.g., similar to a USB flash drive), or substantially cylindrically shaped. It should be noted for purposes of the present disclosure that the term "substantially" should be understood to mean approximately and/or within a certain degree of manufacturing tolerance as would be understood by one skilled in the art. In other implementations, the control body may take another hand-held shape, such as a small box shape, various pod mod (e.g., all-in-one) shapes, or a fob-shape.

In specific implementations, one or both of the control body 102 and the aerosol source member 104 may be referred to as being disposable or as being reusable. For example, the control body 102 may have a replaceable battery or a rechargeable battery, solid-state battery, thin-film solid-state battery, rechargeable supercapacitor or the like, and thus may be combined with any type of recharging technology, including connection to a wall charger, connection to a car charger (e.g., cigarette lighter receptacle, USB port, etc.), connection to a computer, such as through a universal serial bus (USB) cable or connector (e.g., USB 2.0, 3.0, 3.1, USB Type-C), connection to a USB connector (e.g., USB 2.0, 3.0, 3.1, USB Type-C as may be implemented in a wall outlet, electronic device, vehicle, etc.), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger, and connection to an array of external cell(s) such as a power bank to charge a device via a USB connector or a wireless charger. An example of an inductive wireless charging system is described in U.S. Pat. App. Pub. No. 2017/0112196 to Sur et al., which is incorporated herein by reference in its entirety. Further, in some implementations, the aerosol source member 104 may comprise a single-use device. A single use component for use with a control body is disclosed in U.S. Pat. No. 8,910,639 to Chang et al., which is incorporated herein by reference in its entirety. In some implementations, the control body 102 may be inserted into and/or coupled with a separate charging station for charging a rechargeable battery of the device 100. In some implementations, the charging station itself may include a rechargeable power source that recharges the rechargeable battery of the device 100.

Referring to FIG. 2, which illustrates a perspective view of the aerosol delivery device 100 of FIG. 1 wherein the aerosol source member 104 and the control body 102 are decoupled from one another, the aerosol source member 104 of some implementations may comprise a heated end 106, which is configured to be inserted into the control body 102, and a mouth end 108, upon which a user draws to create the aerosol. In various implementations, at least a portion of the heated end 106 may include a substrate portion 110. It should be noted that in other implementations, the aerosol source member 104 need not include a heated end and/or a mouth end.

Figure 3:
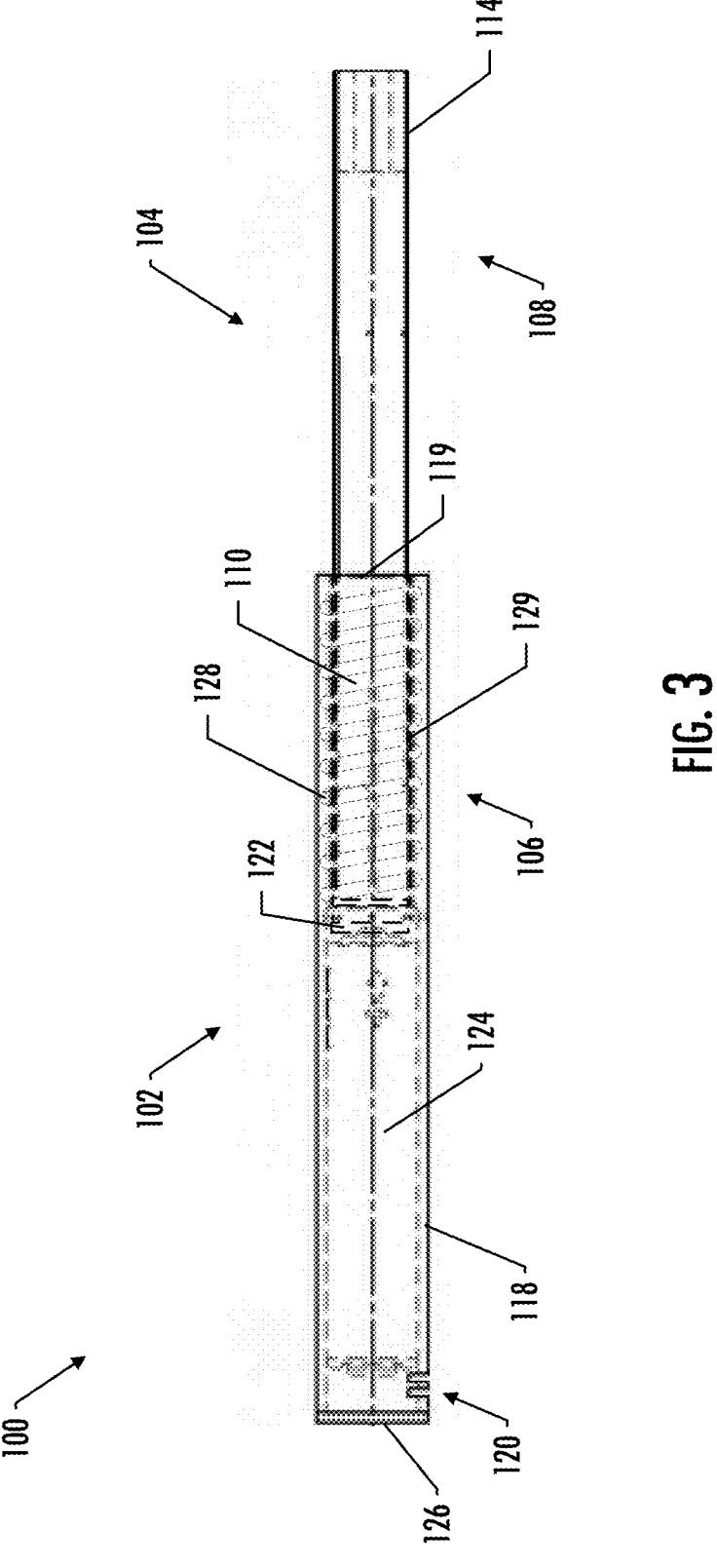
FIG. 3 illustrates a front schematic view of an aerosol delivery device, according to an example implementation of the present disclosure.

As noted above, the heating member of the depicted implementation comprises an inductive heating arrangement. FIG. 3 illustrates a front schematic view of the aerosol delivery device 100 according to an example implementation of the present disclosure. In general, the control body 102 of the depicted implementation includes a resonant transmitter and the aerosol source member 104 includes a resonant receiver (e.g., one or more susceptors, or a plurality of susceptors), which together facilitate heating of at least a portion of the aerosol source member 104 (e.g., the substrate portion 110). Although in various implementations the resonant transmitter and/or the resonant receiver may take a variety of forms, in the particular implementation depicted in FIG. 3, the resonant transmitter comprises a helical coil 128 that, in some implementations may surround a support cylinder 129, although in other implementations there need not be a support cylinder. In various implementations, the resonant transmitter may be made of one or more conductive materials, including, for example, silver, gold, aluminum, brass, zinc, iron, nickel, and alloys of thereof, conductive ceramics e.g., yttrium-doped zirconia, indium tin oxide, yttrium doped titanate, etc, and any combination of the above. In the illustrated implementation, the helical coil 128 is made of a conductive metal material, such as copper. In further implementations, the helical coil may include a non-conductive insulating cover/wrap material. Such materials may include, for example, one or more polymeric materials, such as epoxy, silicon rubber, etc., which may be helpful for low temperature applications, or fiberglass, ceramics, refractory materials, etc., which may be helpful for high temperature applications.

As illustrated, the resonant transmitter 128 may extend proximate an engagement end of the housing 118, and may be configured to substantially surround the portion of the heated end 106 of the aerosol source member 104 that includes the substrate portion 110. In such a manner, the helical coil 128 of the illustrated implementation may define a generally tubular configuration. In some implementations, the support cylinder 129 may also define a tubular configuration and may be configured to support the helical coil 128 such that the helical coil 128 is proximate to but does not contact the substrate portion 110. As such, the support cylinder 129 may comprise a nonconductive material, which may be substantially transparent to an oscillating magnetic field produced by the helical coil 128. In various implementations, the helical coil 128 may be imbedded in, or otherwise coupled to, the support cylinder 129. In the illustrated implementation, the helical coil 128 is engaged with an outer surface of the support cylinder 129; however, in other implementations, the coil may be positioned at an inner surface of the support cylinder, be fully imbedded in the support cylinder, or have some other configuration.

As shown in the figure, the mouth end 108 of the aerosol source member 104 of some implementations may include a filter 114, which, for example, may be made of a cellulose acetate or polypropylene material. In various implementations, the filter 114 may increase the structural integrity of the mouth end 108 of the aerosol source member 100, and/or provide filtering capacity, if desired, and/or provide resistance to draw. For example, an article according to the invention can exhibit a pressure drop of about 50 to about 250 mm water pressure drop at 17.5 cc/second air flow. In further implementations, pressure drop can be about 60 mm to about 180 mm or about 70 mm to about 150 mm. Pressure drop value may be measured using a Filtrona Filter Test Station (CTS Series) available from Filtrona Instruments and Automation Ltd or a Quality Test Module (QTM) available from the Cerulean Division of Molins, PLC. The thickness of the filter along the length of the mouth end of the aerosol source member can vary—e.g., about 2 mm to about 20 mm, about 5 mm to about 20 mm, or about 10 mm to about 15 mm. In some implementations, the filter may comprise discrete segments. For example, some implementations may include a segment providing filtering, a segment providing draw resistance, a hollow segment providing a space for the aerosol to cool, a segment providing increased structural integrity, other filter segments, or any one or any combination of the above.

In various implementations other components may exist between the substrate portion 110 and the mouth end 108 of the aerosol source member 104, wherein the mouth end 108 may include a filter 114. For example, in some implementations one or any combination of the following may be positioned between the substrate portion and the mouth end: an air gap; phase change materials for cooling air; flavor releasing media; ion exchange fibers capable of selective chemical adsorption; aerogel particles as filter medium; and other suitable materials. As noted above, various implementations of the present disclosure employ an inductive heating arrangement to heat a portion of an aerosol source member, such as, for example, the substrate portion of an aerosol source member. The inductive heating arrangement may comprise at least one resonant transmitter and at least one resonant receiver (hereinafter also referred to as a susceptor, or more particularly, a plurality of susceptor particles). In various implementations, the resonant transmitter may be located in the control body and the plurality of susceptor particles may be located in the aerosol source member. Examples of additional possible components that may be included are described in U.S. patent application Ser. No. 15/799,365, filed Oct. 31, 2017, and titled Induction Heated Aerosol Delivery Device, which is incorporated herein by reference in its entirety.

Referring back to FIG. 3, the control body of the depicted implementation 102 may comprise a housing 118 that includes an opening 119 defined in an engaging end thereof, a flow sensor 120 (e.g., a puff sensor or pressure switch), a control component 122 (e.g., a microprocessor, individually or as part of a microcontroller, a printed circuit board (PCB) that includes a microprocessor and/or microcontroller, etc.), a power source 124 (e.g., a battery, which may be rechargeable, and/or a rechargeable supercapacitor), and an end cap that may include an indicator 126 (e.g., a light emitting diode (LED)).

Examples of possible power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties. With respect to the flow sensor 120, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference is also made to the control schemes described in U.S. Pat. No. 9,423,152 to Ampolini et al., which is incorporated herein by reference in its entirety. In one implementation, the indicator 126 may comprise one or more light emitting diodes, quantum dot-based light emitting diodes or the like. In some implementations, the indicator 126 may be in communication with the control component 122 and be illuminated, for example, when a user draws on the aerosol source member 104, when coupled to the control body 102, as detected by the flow sensor 120.

In some implementations, an input element may be included with the aerosol delivery device (and may replace or supplement an airflow or pressure sensor). In various implementations, an input may be included to allow a user to control functions of the device and/or for output of information to a user. Any component or combination of components may be utilized as an input for controlling the function of the device. For example, one or more pushbuttons may be used as described in U.S. Pub. No. 2015/

0245658 to Worm et al., which is incorporated herein by reference in its entirety. Likewise, a touchscreen may be used as described in U.S. Pat. App. Pub. No. 2016/0262454, to Sears et al., which is incorporated herein by reference in its entirety. As a further example, components adapted for gesture recognition based on specified movements of the aerosol delivery device may be used as an input. See U.S. Pat. App. Pub. No. 2016/0158782 to Henry et al., which is incorporated herein by reference in its entirety. As still a further example, a capacitive sensor may be implemented on the aerosol delivery device to enable a user to provide input, such as by touching a surface of the device on which the capacitive sensor is implemented.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Other suitable current actuation/deactuation mechanisms may include a temperature actuated on/off switch or a lip pressure actuated switch, or a touch sensor (e.g., capacitive touch sensor) configured to sense contact between a user (e.g., mouth or fingers of user) and one or more surfaces of the aerosol delivery device. An example mechanism that can provide such puff-actuation capability includes a Model 163PC01D36 silicon sensor, manufactured by the Micro-Switch division of Honeywell, Inc., Freeport, Ill. With such sensor, the heating member may be activated rapidly by a change in pressure when the consumer draws on the device. In addition, flow sensing devices, such as those using hot-wire anemometry principles, may be used to cause the energizing of the heating assembly sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. In some implementations, a pressure-sensing tube or other passage providing fluid connection between the puff actuated switch and aerosol source member may be included in the housing so that pressure changes during draw are readily identified by the switch. Other example puff actuation devices that may be useful according to the present disclosure are disclosed in U.S. Pat. Nos. 4,922,901, 4,947,874, and 4,947,874, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

Figure 4:
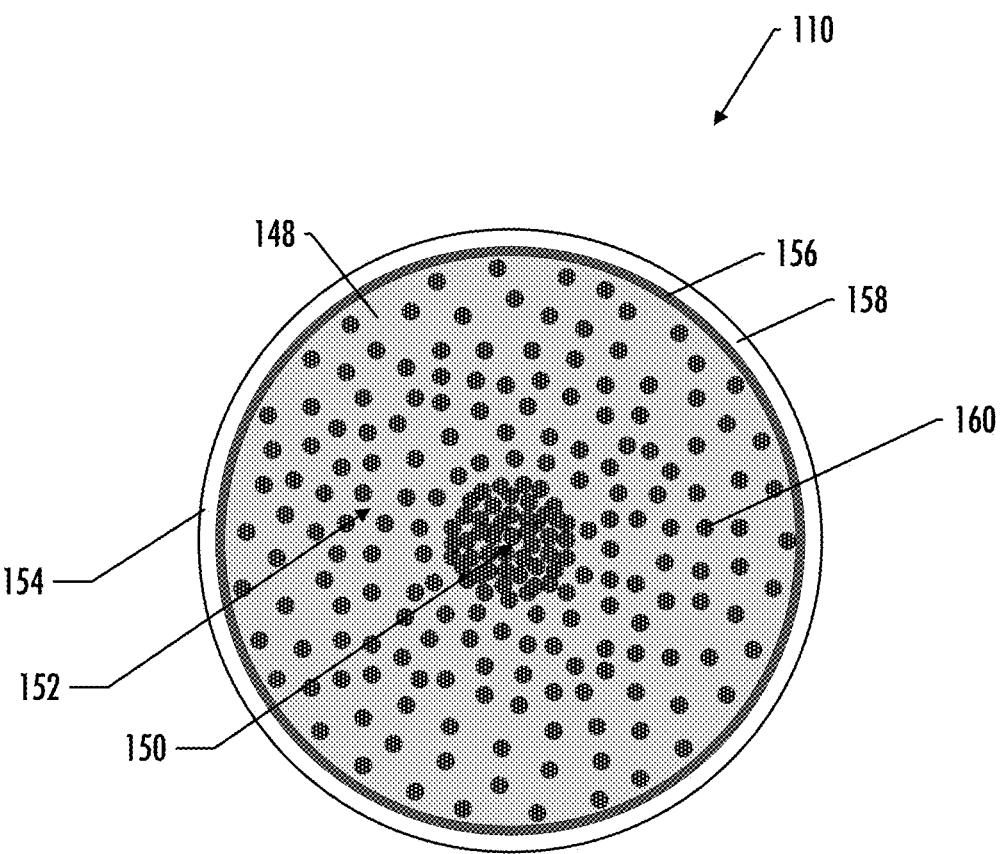
FIG. 4 illustrates a transverse cross-section schematic view of a portion of a substrate portion of an aerosol source member, according to an example implementation of the present disclosure.

FIG. 4 illustrates a cross-section schematic view of a portion of the substrate portion 110 of the aerosol source member 104, according to an example implementation of the present disclosure. In the depicted implementation, the substrate portion 110 of the aerosol source member 104 includes a substrate material 148 comprising a core portion 150, a surrounding portion 152, and a cover layer 154, wherein a plurality of susceptor particles 160 are dispersed within the substrate material 148. In the depicted implementation, the substrate material 148 comprises a single layer that includes the core portion 150 and the surrounding portion 152; however, in other implementations (as will be described in more detail below) the substrate portion 110 may comprise one layer that comprises the core portion and a separate layer that comprises the surrounding portion. In various implementations, the plurality of susceptor particles comprises the resonant receiver of the inductive heating arrangement. In various implementations the substrate material 148 of the depicted implementation may comprise a tobacco material. For example, in some implementations the tobacco material may comprise tobacco-containing beads, tobacco powder, tobacco shreds, tobacco strips, reconstituted tobacco material, a cast tobacco sheet, or combinations thereof, and/or a mix of finely ground tobacco, tobacco extract, spray dried tobacco extract, or other tobacco form mixed with optional inorganic materials (such as calcium carbonate), rice flour, corn flour, carboxymethyl cellulose (CMC), guar gum, alginate, optional flavors, and aerosol forming materials to form a substantially solid or moldable (e.g., extrudable) substrate.

In the depicted implementation, the core portion 150 is located in the approximate radial center of the substrate portion 110, and the surrounding portion 152 is disposed around the core portion 150. In various implementations, the core portion 150 has a diameter that is less than the overall diameter of the substrate portion 110 and may be expressed as a function of the overall diameter of the substrate portion. For example, in some implementations the diameter of the core portion may be approximately ⅛ to ¾ of the overall diameter of the substrate portion, and in some implementations may be approximately ¼ to ½ of the overall diameter of the substrate portion of the aerosol source member. Likewise, the surrounding portion 152 has a diameter that is less than the overall diameter of the substrate portion and may be expressed as a function of the diameter of the core portion. For example, in some implementations the diameter of the surrounding portion may be approximately 1½ to 8 times the diameter of the core portion, and in some implementations, may be approximately 2 to 4 times the diameter of the core portion. In one instance, the diameter of the core portion may be approximately 2 mm and the diameter of the surrounding portion may be in the inclusive range of approximately 6.5 mm to approximately 12 mm.

In various implementations, the core portion 150 of the substrate portion 110 may define a first susceptor particle distribution density, which may generally comprise the relative concentration of susceptor particles 160 within the core portion 150. Likewise, the surrounding portion 152 of the substrate portion 110 may define a second susceptor particle distribution density, which may generally comprise the relative concentration of susceptor particles 160 within the surrounding portion 152. In various implementations, the distribution density of susceptor particles may be defined in a variety of different ways. For example, in some implementations the first distribution density may be defined as the volume of susceptor particles in the core portion as a function of the total volume of the core portion. Likewise, the second distribution density may be defined as the volume of susceptor particles in the surrounding portion as a function of the total volume of the surrounding portion. In other implementations, the first distribution density may be defined as the volume of the susceptor particles in the core portion as a function of the total volume of the substrate portion. Likewise, the second distribution density may be defined as the volume of the susceptor particles in the surrounding portion as a function of the total volume of the substrate portion. In other implementations, the first distribution density may be defined as the area of susceptor particles in the core portion as a function of the total area of the core portion across a cross-section of the substrate portion. Likewise, the second distribution density may be defined as the area of susceptor particles in the surrounding portion as a function of the total area of the surrounding portion across the same cross-section of the substrate portion. In still other implementations wherein the susceptor particles have substantially the same size or fall within the same particle size range, the first distribution density may be defined as the number of susceptor particles in the core portion as a function of the volume of the core portion. Likewise, the second distribution density may be defined as the number of susceptor particles in the surrounding portion as a function of the volume of the surrounding portion.

Regardless of how the distribution densities are calculated, the present disclosure provides that the first distribution density (the distribution density of susceptor particles in the core portion) is greater than the second distribution density (the distribution density of susceptor particles in the surrounding portion). In such a manner, there is a greater concentration of susceptor particles in the core portion than in the surrounding portion. It should be noted that in some implementations, the distribution density of the surrounding portion may be substantially zero, as such, the core portion may include a plurality of susceptor particles but the surrounding portion need not include a plurality of susceptor particles. In one implementation, for example, the volume of the susceptor particles in the core portion may be in the inclusive range of approximately 4% to approximately 8% of the total volume of the substrate portion (including or excluding the cover portion), and the volume of the susceptor particles in the surrounding portion may be in the range of 0% to less than 4% of the total volume of the substrate portion (including or excluding the cover portion).

In some implementations, the substrate material may comprise an extruded tobacco structure. For example, in some implementations the extruded structure may include, or may essentially be comprised of one or more of a tobacco, a tobacco related material, glycerin, water, a binder material, and/or fillers and firming agents, such as, for example, calcium carbonate, rice flour, corn flour, etc. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass.

In some implementations, the substrate material may include an extruded material, as described in U.S. Pat. App. Pub. No. 2012/0042885 to Stone et al., which is incorporated herein by reference in its entirety. In yet another implementation, the substrate material may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings. In other implementations, the extruded material may have two or more sectors, such as, for example, an extrudate with a wagon wheel-like cross section.

Additionally or alternatively, the substrate material may include an extruded structure and/or a substrate that includes or essentially is comprised of tobacco, glycerin, water, and/or binder material, and is further configured to substantially maintain its structure throughout the aerosol-generating process. That is, the substrate material may be configured to substantially maintain its shape (e.g., the substrate material does not continually deform under an applied shear stress) throughout the aerosol-generating process. Although such an example substrate material may include liquids and/or some moisture content, the substrate material may remain substantially solid throughout the aerosol-generating process and may substantially maintain structural integrity throughout the aerosol-generating process. Example tobacco and/or tobacco related materials that may be suitable for a substantially solid substrate material are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In other implementations, the substrate material may comprise a blend of flavorful and aromatic tobaccos in cut filler form. In another implementation, the substrate material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the substrate material may be formed from a wound roll of a reconstituted tobacco material. In another implementation, the substrate material may be formed from shreds, strips, and/or the like of a reconstituted tobacco material. In another implementation, a tobacco sheet may comprise a crimped sheet of reconstituted tobacco material. In some implementations, the substrate material may comprise overlapping layers (e.g., a gathered web), which may, or may not, include heat conducting constituents. Examples of substrate material that include a series of overlapping layers (e.g., gathered webs) of an initial substrate sheet formed by the fibrous filler material, aerosol forming material, and plurality of heat conducting constituents are described in U.S. patent application Ser. No. 15/905,320, filed on Feb. 26, 2018, and titled Heat Conducting Substrate For Electrically Heated Aerosol Delivery Device, which is incorporated herein by reference in its entirety.

In some implementations, the substrate material may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, the substrate material may include a plurality of microcapsules each formed into a hollow cylindrical shape. In some implementations, the substrate material may include a binder material configured to maintain the structural shape and/or integrity of the plurality of microcapsules formed into the hollow cylindrical shape.

Tobacco employed in one or more of the substrate material may include, or may be derived from, tobaccos such as flue-cured tobacco, burley tobacco, Oriental tobacco, Maryland tobacco, dark tobacco, dark-fired tobacco and Rustica tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/0255965 to Perfetti et al.; PCT Pub. No. WO 02/37990 to Bereman; and Bombick et al., *Fund. Appl. Toxicol.,* 39, p. 11-17 (1997); the disclosures of which are incorporated herein by reference in their entireties.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

In some implementations, flame/burn retardant materials and other additives may be included within the substrate material and may include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior. Other examples include diammonium phosphate and/or another salt configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Preferred casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. For example, some flavoring agents may be applied to, or incorporated within, the substrate material and/or those regions of the smoking article where an aerosol is generated. In some implementations, such agents may be supplied directly to a heating cavity or region proximate to the heat source or are provided with the substrate material. Example flavoring agents may include, for example, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, may also be suitable to be employed.

Flavoring agents may also include acidic or basic characteristics (e.g., organic acids, such as levulinic acid, succinic acid, pyruvic acid, and benzoic acid). In some implementations, flavoring agents may be combinable with the elements of the substrate material if desired. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. Any of the materials, such as flavorings, casings, and the like that may be useful in combination with a tobacco material to affect sensory properties thereof, including organoleptic properties, such as described herein, may be combined with the substrate material. Organic acids particularly may be able to be incorporated into the substrate material to affect the flavor, sensation, or organoleptic properties of medicaments, such as nicotine, that may be able to be combined with the substrate material. For example, organic acids, such as levulinic acid, lactic acid, and pyruvic acid, may be included in the substrate material with nicotine in amounts up to being equimolar (based on total organic acid content) with the nicotine. Any combination of organic acids may be suitable. For example, in some implementations, the substrate material may include approximately 0.1 to about 0.5 moles of levulinic acid per one mole of nicotine, approximately 0.1 to about 0.5 moles of pyruvic acid per one mole of nicotine, approximately 0.1 to about 0.5 moles of lactic acid per one mole of nicotine, or combinations thereof, up to a concentration wherein the total amount of organic acid present is equimolar to the total amount of nicotine present in the substrate material. Various additional examples of organic acids that may be employed to produce a substrate material are described in U.S. Pat. App. Pub. No. 2015/0344456 to Dull et al., which is incorporated herein by reference in its entirety.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In some implementations, the substrate material may include other materials having a variety of inherent characteristics or properties. For example, the substrate material may include a plasticized material or regenerated cellulose in the form of rayon. As another example, viscose (commercially available as VISIL®), which is a regenerated cellulose product incorporating silica, may be suitable. Some carbon fibers may include at least 95 percent carbon or more. Similarly, natural cellulose fibers such as cotton may be suitable, and may be infused or otherwise treated with silica, carbon, or metallic particles to enhance flame-retardant properties and minimize off-gassing, particularly of any undesirable off-gassing components that would have a negative impact on flavor (and especially minimizing the likelihood of any toxic off-gassing products). Cotton may be treatable with, for example, boric acid or various organo-phosphate compounds to provide desirable flame-retardant properties by dipping, spraying or other techniques known in the art. These fibers may also be treatable (coated, infused, or both by, e.g., dipping, spraying, or vapor-deposition) with organic or metallic nanoparticles to confer the desired property of flame-retardancy without undesirable off-gassing or melting-type behavior.

As noted, the substrate material may also include an aerosol forming material such as an aerosol precursor composition. In some implementations, the aerosol precursor composition may comprise one or more humectants such as, for example, propylene glycol, glycerin, and/or the like. In various implementations, the amount of the aerosol precursor composition that is used within the aerosol delivery device may be such that the aerosol delivery device exhibits acceptable sensory and organoleptic properties, and desirable performance characteristics. For example, in some implementations the aerosol precursor composition (such as, for example, glycerin and/or propylene glycol), may provide for the generation of a visible mainstream aerosol that in many regards resembles the appearance of tobacco smoke. For example, the amount of aerosol precursor composition incorporated into the substrate material of the smoking article may be in the range of about 4.5 grams or less, 3.5 grams or less, about 3 grams or less, about 2.5 grams or less, about 2 grams or less, about 1.5 grams or less, about 1 gram or less, or about 0.5 gram or less. It should be noted, however, that in other implementations values outside of these ranges are possible.

Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference. In some aspects, an aerosol source member may produce a visible aerosol upon the application of sufficient heat thereto (and cooling with air, if necessary), and the aerosol source member may produce an aerosol that is "smoke-like." In other aspects, the aerosol source member may produce an aerosol that is substantially non-visible but is recognized as present by other characteristics, such as flavor or texture. Thus, the nature of the produced aerosol may be variable depending upon the specific components of the aerosol delivery component. In various implementations, the aerosol source member may be chemically simple relative to the chemical nature of the smoke produced by burning tobacco.

In some implementations, the aerosol precursor composition, also referred to as a vapor precursor composition or "e-liquid," may comprise a variety of components including, by way of example, a polyhydric alcohol (e.g., glycerin, propylene glycol, or a mixture thereof), nicotine, tobacco, tobacco extract, and/or flavorants. Some possible types of aerosol precursor components and formulations are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also possible are the so-called "smoke juices" for electronic cigarettes that have been available from Johnson Creek Enterprises LLC. Still further examples of possible aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol source member is such that the aerosol generating piece provides acceptable sensory and desirable performance characteristics. For example, it is desired that sufficient amounts of aerosol forming material be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 0.5 ml or more, about 1 ml or more, about 2 ml or more, about 5 ml or more, or about 10 ml or more of the aerosol precursor composition may be included.

Referring back to FIG. 4, as noted above the core portion 150 and the surrounding portion 152 include a plurality of susceptor particles 160, which comprise the resonant receiver of the inductive heating arrangement of the depicted implementation. In various implementations, the plurality of susceptor particles 160 may have a variety of shapes, sizes, and materials, which, in some implementations, may be combined within the same substrate portion. For example, in some implementations one or more of the plurality of susceptor particles 160 may have a substantially spherical shape, a flake-like shape, a substantially cubic shape, an irregular shape (such as, for example, a shape having one or more (e.g., multiple) sides with differing dimensions), or any combinations thereof. In various implementations, the plurality of susceptor particles 160 may comprise a ferromagnetic material including, but not limited to, cobalt, iron, nickel, zinc, manganese, and any combinations thereof. In additional implementations, the plurality of susceptor particles 160 may comprise other materials, including, for example, other porous metal materials such as aluminum or stainless steel, as well as ceramic materials such as silicon carbide, carbon materials, and any combinations of any of the materials described above. In still other implementations, the plurality of susceptor particles may comprise other conductive materials including metals such as copper, alloys of conductive materials, or other materials with one or more conductive materials imbedded therein. Although in various implementations, the size of a porous susceptor particle may vary, in some implementations one or more of the plurality of porous susceptor particles may have a diameter in the inclusive range of approximately 100 microns (0.1 mm) to approximately 2 mm, and in some implementations, one or more of the plurality of porous susceptor particles may have a diameter in the inclusive range of approximately 0.5 mm to approximately 1.5 mm.

In the depicted implementation, a change in current in the helical coil 128 (i.e., the resonant transmitter), as directed thereto from the power source 124 by the control component 122 (e.g., via a driver circuit) may produce an alternating electromagnetic field that penetrates the plurality of susceptor particles 160 (i.e., the resonant receiver), thereby generating electrical eddy currents within the plurality of susceptor particles 160. The alternating electromagnetic field may be produced by directing alternating current to the helical coil 128. As noted above, in some implementations, the control component 122 may include an inverter or inverter circuit configured to transform direct current provided by the power source to alternating current that is provided to the resonant transmitter.

The eddy currents flowing in the plurality of susceptor particles 160 may generate heat through the Joule effect, wherein the amount of heat produced is proportional to the square of the electrical current times the electrical resistance of the material of the plurality of susceptor particles 160. For implementations wherein the plurality of susceptor particles 160 comprises ferromagnetic materials, heat may also be generated by magnetic hysteresis losses. Several factors contribute to the temperature rise of the plurality of susceptor particles 160 including, but not limited to, proximity to the helical coil 128, distribution of the magnetic field, electrical resistivity of the material of the plurality of susceptor particles 160, saturation flux density, skin effects or depth, hysteresis losses, magnetic susceptibility, magnetic permeability, and dipole moment of the material.

In this regard and as noted above, both the plurality of susceptor particles 160 and the helical coil 128 may comprise an electrically conductive material. By way of example, the helical coil 128 and/or the plurality of susceptor particles 160 may comprise various conductive materials including metals such as copper or aluminum, alloys of conductive materials (e.g., diamagnetic, paramagnetic, or ferromagnetic materials) or other materials such as a ceramic or glass with one or more conductive materials imbedded therein. In some implementations, the plurality of susceptor particles may be coated with or otherwise include a thermally conductive passivation layer (e.g., a thin layer of glass).

In some implementations, the plurality of porous susceptor particles 160 contained in the aerosol source member 104 may be supplemented with an additional/alternate resonant receiver. For example, in some implementations the control body 102 of the device 100 may include a separate resonant receiver such as, for example, one or more receiver prongs. Some examples of suitable components are described in U.S. patent application Ser. No. 15/799,365, filed Oct. 31, 2017, and titled Induction Heated Aerosol Delivery Device, which is incorporated herein by reference in its entirety.

Referring back to FIG. 4, the substrate portion 110 of the some implementations may also include a cover layer 154 that is disposed around the surrounding portion 152. In the depicted implementation, the cover layer 154 comprises a foil sublayer 156 and a paper sublayer 158, wherein the paper sublayer 158 is disposed around the foil sublayer 156. In some implementations, the foil and paper sublayers may comprise a single laminate. In some implementations, the paper sublayer may comprise a paper or other fibrous material, such as a cellulose material. The paper sublayer material may also include at least one filler material imbedded or dispersed within the fibrous material. In various implementations, the filler material may have the form of water insoluble particles. Additionally, the filler material may incorporate inorganic components. In some implementations, the paper sublayer may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. Various types of paper materials are described in U.S. Pat. No. 5,105,838 to White et al.; 5,271,419 to Arzonico et al.; 5,220,930 to Gentry; 6,908,874 to Woodhead et al.; 6,929,

24

013 to Ashcraft et al.; 7,195,019 to Hancock et al.; 7,276,120 to Holmes; 7,275,548 to Hancock et al.; PCT WO 01/08514 to Fournier et al.; and PCT WO 03/043450 to Hajaligol et al., which are incorporated herein by reference in their entireties. In some implementations, the paper material may comprise a commercially available material such as R. J. Reynolds Tobacco Company Grades 119, 170, 419, 453, 454, 456, 465, 466, 490, 525, 535, 557, 652, 664, 672, 676 and 680 from Schweitzer-Maudit International. In the depicted implementation, the foil sublayer 152 comprises a metal foil material, such as an aluminum foil material. In other implementations, however, the foil sublayer may comprise other materials, including, but not limited to, copper materials, tin materials, gold materials, graphene materials, graphite materials, or other thermally conductive carbon-based materials, and/or any combinations thereof. Although a variety of thicknesses are possible, in some implementations the cover layer may have a thickness in the inclusive range of approximately 1 mm to approximately 3 mm.

Figure 5:
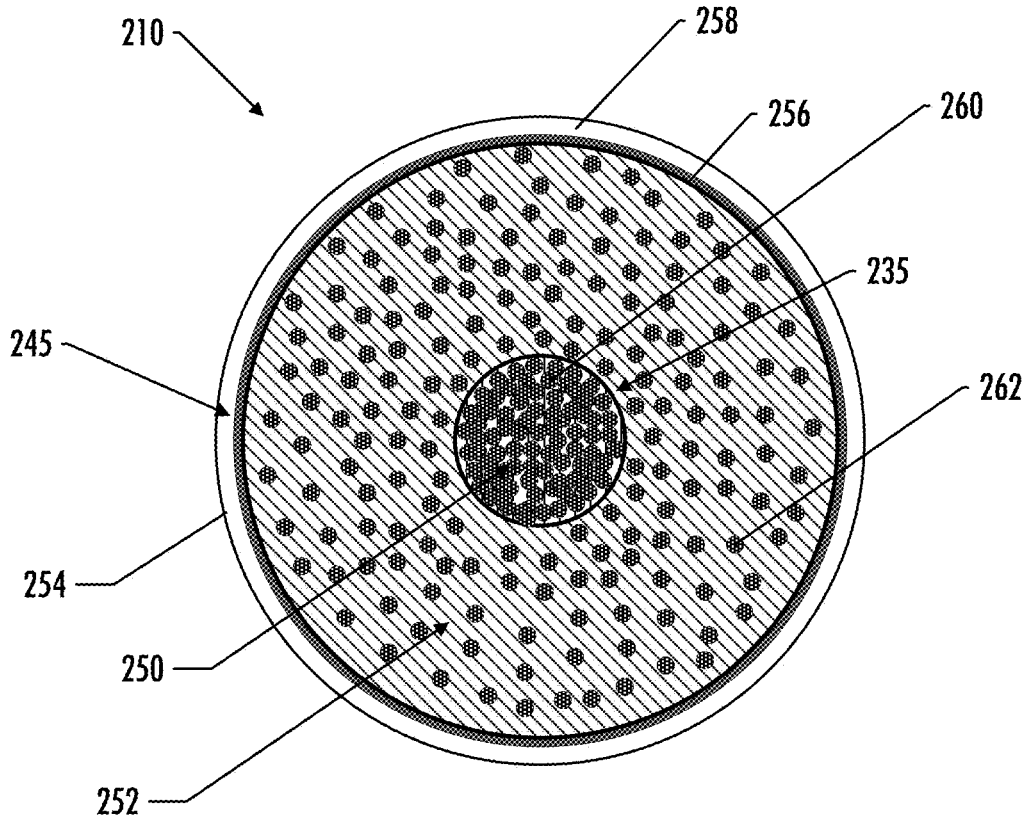
FIG. 5 illustrates a transverse cross-section schematic view of a portion of a substrate portion of an aerosol source member, according to an example implementation of the present disclosure.

An alternate implementation of the present disclosure is illustrated in FIG. 5. In particular, FIG. 5 illustrates a cross-section schematic view of a portion of a substrate portion 210 of an aerosol source member according to another example implementation of the present disclosure. In various implementations, an aerosol source member having the substrate portion 210 of FIG. 5 may be usable with various control bodies, such as, for example, the control bodies of FIGS. 1-3 and 10. In the depicted implementation, the substrate portion 210 of the aerosol source member comprises multiple layers. For example, in the depicted implementation the substrate portion 210 includes a first layer 235 that comprises a core portion 250 and second layer 245 that comprises a surrounding portion 252. In the depicted implementation, the first layer 235 is located in the approximate radial center of the substrate portion 210 and the second layer 245 is disposed around the first layer 235. In some implementations, the first layer 235 has a diameter that is less than the overall diameter of the substrate portion 210 and may be expressed as a function of the overall diameter of the substrate portion. For example, in some implementations the diameter of the core portion may be approximately ⅛ to ¾ of the overall diameter of the substrate portion, and in some implementations may be approximately ¼ to ½ of the overall diameter of the substrate portion of the aerosol source member. Likewise, the surrounding portion 152 has a diameter that is less than the overall diameter of the substrate portion and may be expressed as a function of the diameter of the core portion. For example, in some implementations the diameter of the surrounding portion may be approximately 1½ to 8 times the diameter of the core portion, and in some implementations, may be approximately 2 to 4 times the diameter of the core portion. In one instance, the diameter of the core portion may be approximately 2 mm and the diameter of the surrounding portion may be in the inclusive range of approximately 6.5 mm to approximately 12 mm.

In various implementations, the first layer 235 comprising the core portion 250 may define a first susceptor particle distribution density, which may generally comprise the relative concentration of susceptor particles within the first layer 235. Likewise, the second layer 245 comprising the surrounding portion 252 may define a second susceptor particle distribution density, which may generally comprise the relative concentration of susceptor particles within the second layer 245. In various implementations, the distribution density of susceptor particles may be defined in a variety of different ways. For example, in some implementations the first distribution density may be defined as the volume of susceptor particles in the first layer as a function of the total volume of the first layer. Likewise, the second distribution density may be defined as the volume of susceptor particles in the second layer as a function of the total volume of the second layer. In other implementations, the first distribution density may be defined as the volume of the susceptor particles in the first layer as a function of the total volume of the substrate portion. Likewise, the second distribution density may be defined as the volume of the susceptor particles in the second layer as a function of the total volume of the substrate portion. In other implementations, the first distribution density may be defined as the area of susceptor particles in the first layer as a function of the total area of the first layer across a cross-section of the substrate portion. Likewise, the second distribution density may be defined as the area of susceptor particles in the second layer as a function of the total area of the second layer across the same cross-section of the substrate portion. In still other implementations wherein the susceptor particles have substantially the same size or fall within the same particle size range, the first distribution density may be defined as the number of susceptor particles in the first layer as a function of the volume of the first layer. Likewise, the second distribution density may be defined as the number of susceptor particles in the second layer as a function of the volume of the second layer.

Regardless of how the distribution densities are calculated, the present disclosure provides that the first distribution density (the distribution density of susceptor particles in the first layer comprising the core portion) is greater than the second distribution density (the distribution density of susceptor particles in the second layer comprising the surrounding portion). In such a manner, there is a greater concentration of susceptor particles in the core portion than in the surrounding portion. It should be noted that in the depicted implementation, the susceptor particles 260 of the first layer 235 and the susceptor particles 262 of the second layer 245 comprise substantially the same type of particles (e.g., substantially the same material); however, in other implementations, the type of susceptor particles of the first layer may be different than the type of susceptor particles the second layer. In still other implementations, the first layer may include a plurality of susceptor particles, but the second layer need not include a plurality of susceptor particles. In one implementation, for example, the volume of the susceptor particles in the first layer may be in the inclusive range of approximately 4% to approximately 8% of the total volume of the substrate portion (including or excluding the cover portion), and the volume of the susceptor particles in the second layer may be in the range of 0% to less than 4% of the total volume of the substrate portion (including or excluding the cover portion).

In the depicted implementation, the first layer 235 and/or the second layer 245 may comprise a substrate material. In some implementations, the substrate material may comprise an extruded tobacco structure. For example, in some implementations the extruded structure may include, or may essentially be comprised of one or more of a tobacco, a tobacco related material, glycerin, water, a binder material, and/or fillers and firming agents, such as, for example, calcium carbonate, rice flour, corn flour, etc. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions.

Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass.

In some implementations, the substrate material may include an extruded material, as described in U.S. Pat. App. Pub. No. 2012/0042885 to Stone et al., which is incorporated herein by reference in its entirety. In yet another implementation, the substrate material may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings. In other implementations, the extruded material may have two or more sectors, such as, for example, an extrudate with a wagon wheel-like cross section.

Additionally or alternatively, the substrate material may include an extruded structure and/or a substrate that includes or essentially is comprised of tobacco, glycerin, water, and/or binder material, and is further configured to substantially maintain its structure throughout the aerosol-generating process. That is, the substrate material may be configured to substantially maintain its shape (e.g., the substrate material does not continually deform under an applied shear stress) throughout the aerosol-generating process. Although such an example substrate material may include liquids and/or some moisture content, the substrate material may remain substantially solid throughout the aerosol-generating process and may substantially maintain structural integrity throughout the aerosol-generating process. Example tobacco and/or tobacco related materials that may be suitable for a substantially solid substrate material are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In other implementations, the substrate material may comprise a blend of flavorful and aromatic tobaccos in cut filler form. In another implementation, the substrate material may comprise a reconstituted tobacco material, such as described in U.S. Pat. No. 4,807,809 to Pryor et al.; U.S. Pat.

No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the substrate material may be formed from a wound roll of a reconstituted tobacco material. In another implementation, the substrate material may be formed from shreds, strips, and/or the like of a reconstituted tobacco material. In another implementation, the tobacco sheet may comprise a crimped sheet of reconstituted tobacco material. In some implementations, the substrate material may comprise overlapping layers (e.g., a gathered web), which may, or may not, include heat conducting constituents. Examples of substrate material that include a series of overlapping layers (e.g., gathered webs) of an initial substrate sheet formed by the fibrous filler material, aerosol forming material, and plurality of heat conducting constituents are described in U.S. patent application Ser. No. 15/905,320, filed on Feb. 26, 2018, and titled Heat Conducting Substrate For Electrically Heated Aerosol Delivery Device, which is incorporated herein by reference in its entirety.

In some implementations, the substrate material may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, the substrate material may include a plurality of microcapsules each formed into a hollow cylindrical shape. In some implementations, the substrate material may include a binder material configured to maintain the structural shape and/or integrity of the plurality of microcapsules formed into the hollow cylindrical shape.

Tobacco employed in one or more of the substrate material may include, or may be derived from, tobaccos such as flue-cured tobacco, burley tobacco, Oriental tobacco, Maryland tobacco, dark tobacco, dark-fired tobacco and Rustica tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/0255965 to Perfetti et al.; PCT Pub. No. WO 02/37990 to Bereman; and Bombick et al., Fund. Appl. Toxicol., 39, p. 11-17 (1997); the disclosures of which are incorporated herein by reference in their entireties.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

In some implementations, flame/burn retardant materials and other additives may be included within the substrate material and may include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior. Other examples include diammonium phosphate and/or another salt configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Preferred casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. For example, some flavoring agents may be applied to, or incorporated within, the substrate material and/or those regions of the smoking article where an aerosol is generated. In some implementations, such agents may be supplied directly to a heating cavity or region proximate to the heat source or are provided with the substrate material. Example flavoring agents may include, for example, vanillin, ethyl vanillin, cream, tea, coffee, fruit (e.g., apple, cherry, straw-berry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, may also be suitable to be employed.

Flavoring agents may also include acidic or basic char-acteristics (e.g., organic acids, such as levulinic acid, suc-cinic acid, pyruvic acid, and benzoic acid). In some imple-mentations, flavoring agents may be combinable with the elements of the substrate material if desired. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. Any of the materials, such as flavorings, casings, and the like that may be useful in combination with a tobacco material to affect sensory properties thereof, including organoleptic properties, such as described herein, may be combined with the substrate material. Organic acids particularly may be able to be incorporated into the substrate material to affect the flavor, sensation, or organoleptic properties of medica-ments, such as nicotine, that may be able to be combined with the substrate material. For example, organic acids, such as levulinic acid, lactic acid, and pyruvic acid, may be included in the substrate material with nicotine in amounts up to being equimolar (based on total organic acid content) with the nicotine. Any combination of organic acids may be suitable. For example, in some implementations, the sub-strate material may include approximately 0.1 to about 0.5 moles of levulinic acid per one mole of nicotine, approxi-mately 0.1 to about 0.5 moles of pyruvic acid per one mole of nicotine, approximately 0.1 to about 0.5 moles of lactic acid per one mole of nicotine, or combinations thereof, up to a concentration wherein the total amount of organic acid present is equimolar to the total amount of nicotine present in the substrate material. Various additional examples of organic acids that may be employed to produce a substrate material are described in U.S. Pat. App. Pub. No. 2015/0344456 to Dull et al., which is incorporated herein by reference in its entirety.

The selection of such further components may be variable based upon factors such as the sensory characteristics that are desired for the smoking article, and the present disclo-sure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In some implementations, the substrate material may include other materials having a variety of inherent characteristics or properties. For example, the substrate material may include a plasticized material or regenerated cellulose in the form of rayon. As another example, viscose (com-mercially available as VISIL®), which is a regenerated cellulose product incorporating silica, may be suitable. Some carbon fibers may include at least 95 percent carbon or more. Similarly, natural cellulose fibers such as cotton may be suitable, and may be infused or otherwise treated with silica, carbon, or metallic particles to enhance flame-retardant properties and minimize off-gassing, particularly of any undesirable off-gassing components that would have a negative impact on flavor (and especially minimizing the likelihood of any toxic off-gassing products). Cotton may be treatable with, for example, boric acid or various organo-phosphate compounds to provide desirable flame-retardant properties by dipping, spraying or other techniques known in the art. These fibers may also be treatable (coated, infused, or both by, e.g., dipping, spraying, or vapor-deposition) with organic or metallic nanoparticles to confer the desired prop-erty of flame-retardancy without undesirable off-gassing or melting-type behavior.

In the depicted implementation, the first layer and/or the second layer may also include an aerosol forming material such as an aerosol precursor composition. In some imple-mentations, the aerosol precursor composition may com-prise one or more humectants such as, for example, propyl-ene glycol, glycerin, and/or the like. In various implementations, the amount of the aerosol precursor com-position that is used within the aerosol delivery device may be such that the aerosol delivery device exhibits acceptable sensory and organoleptic properties, and desirable perfor-mance characteristics. For example, in some implementa-tions the aerosol precursor composition (such as, for example, glycerin and/or propylene glycol), may provide for the generation of a visible mainstream aerosol that in many regards resembles the appearance of tobacco smoke. For example, the amount of aerosol precursor composition incorporated into the substrate material of the smoking article may be in the range of about 4.5 grams or less, 3.5 grams or less, about 3 grams or less, about 2.5 grams or less, about 2 grams or less, about 1.5 grams or less, about 1 gram or less, or about 0.5 gram or less. It should be noted, however, that in other implementations values outside of these ranges are possible.

Representative types of further aerosol precursor compo-sitions are set forth in U.S. Pat. No. 4,793,365 to Sensa-baugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Mono-graph (1988); the disclosures of which are incorporated herein by reference. In some aspects, an aerosol source member may produce a visible aerosol upon the application of sufficient heat thereto (and cooling with air, if necessary), and the aerosol source member may produce an aerosol that is "smoke-like." In other aspects, the aerosol source member may produce an aerosol that is substantially non-visible but is recognized as present by other characteristics, such as flavor or texture. Thus, the nature of the produced aerosol may be variable depending upon the specific components of the aerosol delivery component. In various implementations, the aerosol source member may be chemically simple rela-tive to the chemical nature of the smoke produced by burning tobacco.

In some implementations, the aerosol precursor compo-sition, also referred to as a vapor precursor composition or "e-liquid," may comprise a variety of components including, by way of example, a polyhydric alcohol (e.g., glycerin, propylene glycol, or a mixture thereof), nicotine, tobacco, tobacco extract, and/or flavorants. Some possible types of aerosol precursor components and formulations are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also possible are the so-called "smoke juices" for electronic cigarettes that have been available from Johnson Creek Enterprises LLC. Still further examples of possible aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQ-UID, SMILEY E LIQUID, BEANTOWN VAPOR, CUTT-WOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol source member is such that the aerosol generating piece provides acceptable sensory and desirable performance characteristics. For example, it is desired that sufficient amounts of aerosol forming material be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 0.5 ml or more, about 1 ml or more, about 2 ml or more, about 5 ml or more, or about 10 ml or more of the aerosol precursor composition may be included.

Referring back to FIG. 5, as noted above the first layer 235 includes a plurality of susceptor particles 260, and the second layer 252 includes a plurality of susceptor particles 262, wherein the susceptor particles 260, 262 comprise the resonant receiver. In various implementations, the plurality of susceptor particles 260, 262 may have a variety of shapes, sizes, and materials, which, in some implementations, may be combined within the same layer. For example, in some implementations one or more of the plurality of susceptor particles 260, 262 may have a substantially spherical shape, a flake-like shape, a substantially cubic shape, an irregular shape (such as, for example, a shape having one or more (e.g., multiple) sides with differing dimensions), or any combinations thereof. In various implementations, the plurality of susceptor particles 260, 262 may comprise a ferromagnetic material including, but not limited to, cobalt, iron, nickel, zinc, manganese, and any combinations thereof. In additional implementations, the plurality of susceptor particles 260, 262 may comprise other materials, including, for example, other porous metal materials such as aluminum or stainless steel, as well as ceramic materials such as silicon carbide, carbon materials, and any combinations of any of the materials described above. In still other implementations, the plurality of susceptor particles may comprise other conductive materials including metals such as copper, alloys of conductive materials, or other materials with one or more conductive materials imbedded therein. Although in various implementations, the size of a porous susceptor particle may vary, in some implementations one or more of the plurality of porous susceptor particles may have a diameter in the inclusive range of approximately 100 microns (0.1 mm) to approximately 2 mm, and in some implementations, one or more of the plurality of porous susceptor particles may have a diameter in the inclusive range of approximately 0.5 mm to approximately 1.5 mm.

In the depicted implementation, a change in current in the helical coil of the control body (i.e., the resonant transmitter), as directed thereto from the power source by the control component (e.g., via a driver circuit) may produce an alternating electromagnetic field that penetrates the plurality of susceptor particles 260, 262 (i.e., the resonant receiver), thereby generating electrical eddy currents within the plurality of susceptor particles 260, 262. The alternating electromagnetic field may be produced by directing alternating current to the helical coil. As noted above, in some implementations, the control component may include an inverter or inverter circuit configured to transform direct current provided by the power source to alternating current that is provided to the resonant transmitter.

The eddy currents flowing in the plurality of susceptor particles 260, 262 may generate heat through the Joule effect, wherein the amount of heat produced is proportional to the square of the electrical current times the electrical resistance of the material of the plurality of susceptor particles 260, 262. For implementations wherein the plurality of susceptor particles 260, 262 comprises ferromagnetic materials, heat may also be generated by magnetic hysteresis losses. Several factors contribute to the temperature rise of the plurality of susceptor particles 260, 262 including, but not limited to, proximity to the helical coil, distribution of the magnetic field, electrical resistivity of the material of the plurality of susceptor particles 260, 262, saturation flux density, skin effects or depth, hysteresis losses, magnetic susceptibility, magnetic permeability, and dipole moment of the material.

In this regard and as noted above, both the plurality of susceptor particles 260, 262 and the helical coil may comprise an electrically conductive material. By way of example, the helical coil and/or the plurality of susceptor particles 260, 262 may comprise various conductive materials including metals such as copper or aluminum, alloys of conductive materials (e.g., diamagnetic, paramagnetic, or ferromagnetic materials) or other materials such as a ceramic or glass with one or more conductive materials imbedded therein. In some implementations, the plurality of susceptor particles may be coated with or otherwise include a thermally conductive passivation layer (e.g., a thin layer of glass).

In some implementations, the plurality of porous susceptor particles 260, 262 contained in the aerosol source member may be supplemented with an additional/alternate resonant receiver. For example, in some implementations the control body of the device may include a separate resonant receiver such as, for example, one or more receiver prongs. Examples of suitable components are described in U.S. patent application Ser. No. 15/799,365, filed Oct. 31, 2017, which is incorporated herein by reference in its entirety.

Referring back to FIG. 5, the substrate portion 210 of some implementations may also include a cover layer 254 that is disposed around the surrounding portion 252. In the depicted implementation, the cover layer 254 comprises a foil sublayer 256 and a paper sublayer 258, wherein the paper sublayer 258 is disposed around the foil sublayer 256. In some implementations, the foil and paper sublayers may comprise a single laminate. In some implementations, the paper sublayer may comprise a paper or other fibrous material, such as a cellulose material. The paper sublayer material may also include at least one filler material imbedded or dispersed within the fibrous material. In various implementations, the filler material may have the form of water insoluble particles. Additionally, the filler material may incorporate inorganic components. In some implementations, the paper sublayer may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. Various types of paper materials are described in U.S. Pat. No. 5,105,838 to White et al.; 5,271,419 to Arzonico et al.; 5,220,930 to Gentry; 6,908,874 to Woodhead et al.; 6,929, 013 to Ashcraft et al.; 7,195,019 to Hancock et al.; 7,276,120 to Holmes; 7,275,548 to Hancock et al.; PCT WO 01/08514 to Fournier et al.; and PCT WO 03/043450 to Hajaligol et al., which are incorporated herein by reference in their entireties. In some implementations, the paper material may comprise a commercially available material such as R. J. Reynolds Tobacco Company Grades 119, 170, 419, 453, 454, 456, 465, 466, 490, 525, 535, 557, 652, 664, 672, 676 and 680 from Schweitzer-Maudit International. In the depicted implementation, the foil sublayer 252 comprises a metal foil material, such as an aluminum foil material. In other implementations, however, the foil sublayer may comprise other materials, including, but not limited to, a copper material, a tin material, a gold material, a graphene material, a graphite material or other thermally conductive carbon-based material, and/or any combinations thereof. Although a variety of thicknesses are possible, in some implementations the cover layer may have a thickness in the inclusive range of approximately 1 mm to approximately 3 mm.

Figure 6:
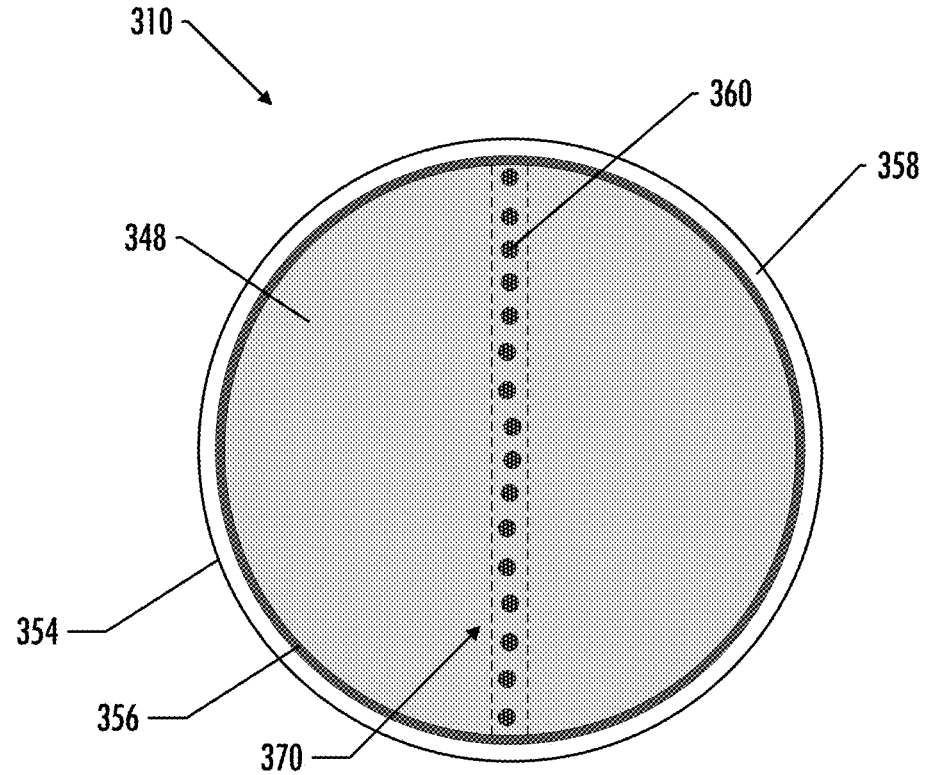
FIG. 6 illustrates a transverse cross-section schematic view of a portion of a substrate portion of an aerosol source member, according to an example implementation of the present disclosure.
Figure 7:
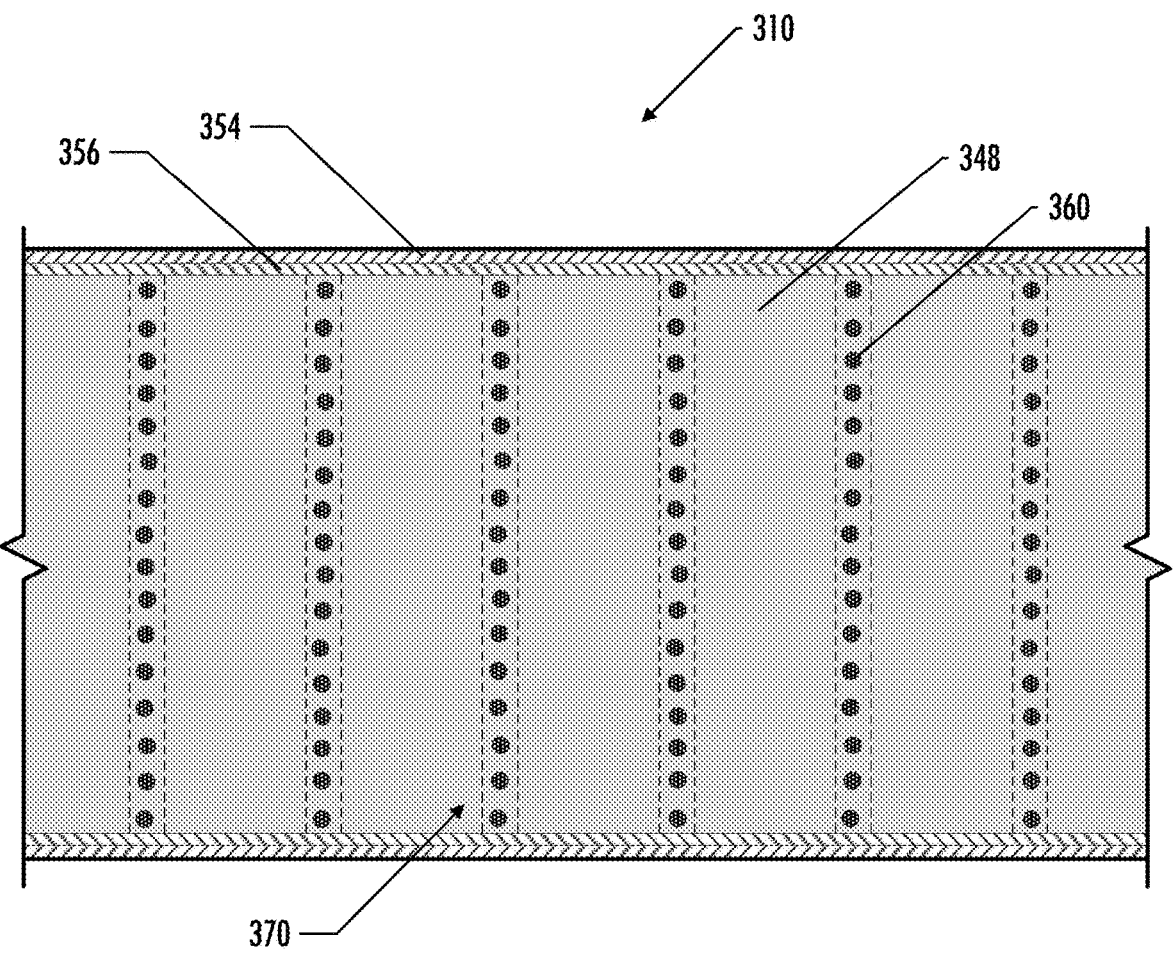
FIG. 7 illustrates a longitudinal cross-section schematic view of a portion of the substrate portion of the aerosol source member of FIG. 6, according to an example implementation of the present disclosure.

An alternate implementation of the present disclosure is illustrated in FIGS. 6 and 7. In particular, FIG. 6 illustrates a transverse cross-section schematic view of a portion of a substrate portion 310 of an aerosol source member, and FIG. 7 illustrates a longitudinal cross-section schematic view of a portion of the substrate portion 310 of the aerosol source member of FIG. 6. In various implementations, an aerosol source member having the substrate portion 310 of FIGS. 6 and 7 may be usable with various control bodies, such as, for example, the control bodies of FIGS. 1-3 and 10. In the depicted implementation, the substrate portion 310 of the aerosol source member includes a plurality of a plurality of susceptor bands 370 (see FIG. 7) that extend through at least a portion of the substrate portion 310. In various implementations, the number of susceptor bands in the substrate portion 310 may vary. For example, in some implementations there may be as few as two susceptor bands, and in other implementations there may be as many as twelve, or more, susceptor bands. Although other configurations are possible, in the depicted implementation the plurality of susceptor bands 370 are spaced along a length of the substrate portion 310. In particular, the plurality of susceptor bands 370 of the depicted implementation are substantially evenly spaced along a length of the substrate portion 310. In various implementations, a plurality of susceptor particles 360 are located within each susceptor band 370. Although other configurations are possible, in the depicted implementation the plurality of susceptor particles 360 are substantially aligned and substantially evenly spaced within each susceptor band 370.

In the depicted implementation, the plurality of susceptor bands 370 extend through the center of the substrate portion 310 and across a diameter thereof, the substrate portion 310 of the depicted implementation comprises a substrate material 348, and the plurality of susceptor particles 360 are imbedded in or dispersed within the substrate material 348. In some implementations, the substrate material may comprise an extruded tobacco structure. For example, in some implementations the extruded structure may include, or may essentially be comprised of one or more of a tobacco, a tobacco related material, glycerin, water, a binder material, and/or fillers and firming agents, such as, for example, calcium carbonate, rice flour, corn flour, etc. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass.

In some implementations, the substrate material may include an extruded material, as described in U.S. Pat. App. Pub. No. 2012/0042885 to Stone et al., which is incorporated herein by reference in its entirety. In yet another implementation, the substrate material may include an extruded structure and/or substrate formed from marumarized and/or non-marumarized tobacco. Marumarized tobacco is known, for example, from U.S. Pat. No. 5,105, 831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings. In other implementations, the extruded material may have two or more sectors, such as, for example, an extrudate with a wagon wheel-like cross section.

Additionally or alternatively, the substrate material may include an extruded structure and/or a substrate that includes or essentially is comprised of tobacco, glycerin, water, and/or binder material, and is further configured to substantially maintain its structure throughout the aerosol-generating process. That is, the substrate material may be configured to substantially maintain its shape (e.g., the substrate material does not continually deform under an applied shear stress) throughout the aerosol-generating process. Although such an example substrate material may include liquids and/or some moisture content, the substrate material may remain substantially solid throughout the aerosol-generating process and may substantially maintain structural integrity throughout the aerosol-generating process. Example tobacco and/or tobacco related materials that may be suitable for a substantially solid substrate material are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In other implementations, the substrate material may comprise a blend of flavorful and aromatic tobaccos in cut filler form. In another implementation, the substrate material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the substrate material may be formed from a wound roll of a reconstituted tobacco material. In another implementation, the substrate material may be formed from shreds, strips, and/or the like of a reconstituted tobacco material. In another implementation, the tobacco sheet may comprise a crimped sheet of reconstituted tobacco material. In some implementations, the substrate material may comprise overlapping layers (e.g., a gathered web), which may, or may not, include heat conducting constituents. Examples of substrate material that include a series of overlapping layers (e.g., gathered webs) of an initial substrate sheet formed by the fibrous filler material, aerosol forming material, and plurality of heat conducting constituents are described in U.S. patent application Ser. No. 15/905,320, filed on Feb. 26, 2018, and titled Heat Conducting Substrate For Electrically Heated Aerosol Delivery Device, which is incorporated herein by reference in its entirety.

In some implementations, the substrate material may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, the substrate material may include a plurality of microcapsules each formed into a hollow cylindrical shape. In some implementations, the substrate material may include a binder material configured to maintain the structural shape and/or integrity of the plurality of microcapsules formed into the hollow cylindrical shape.

Tobacco employed in one or more of the substrate material may include, or may be derived from, tobaccos such as flue-cured tobacco, burley tobacco, Oriental tobacco, Maryland tobacco, dark tobacco, dark-fired tobacco and Rustica tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/0255965 to Perfetti et al.; PCT Pub. No. WO 02/37990 to Bereman; and Bombick et al., *Fund. Appl. Toxicol.*, 39, p. 11-17 (1997); the disclosures of which are incorporated herein by reference in their entireties.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

In some implementations, flame/burn retardant materials and other additives may be included within the substrate material and may include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior. Other examples include diammonium phosphate and/or another salt configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Preferred casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. For example, some flavoring agents may be applied to, or incorporated within, the substrate material and/or those regions of the smoking article where an aerosol is generated. In some implementations, such agents may be supplied directly to a heating cavity or region proximate to the heat source or are provided with the substrate material. Example flavoring agents may include, for example, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, may also be suitable to be employed.

Flavoring agents may also include acidic or basic characteristics (e.g., organic acids, such as levulinic acid, succinic acid, pyruvic acid, and benzoic acid). In some implementations, flavoring agents may be combinable with the elements of the substrate material if desired. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. Any of the materials, such as flavorings, casings, and the like that may be useful in combination with a tobacco material to affect sensory properties thereof, including organoleptic properties, such as described herein, may be combined with the substrate material. Organic acids particularly may be able to be incorporated into the substrate material to affect the flavor, sensation, or organoleptic properties of medicaments, such as nicotine, that may be able to be combined with the substrate material. For example, organic acids, such as levulinic acid, lactic acid, and pyruvic acid, may be included in the substrate material with nicotine in amounts up to being equimolar (based on total organic acid content) with the nicotine. Any combination of organic acids may be suitable. For example, in some implementations, the substrate material may include approximately 0.1 to about 0.5 moles of levulinic acid per one mole of nicotine, approximately 0.1 to about 0.5 moles of pyruvic acid per one mole of nicotine, approximately 0.1 to about 0.5 moles of lactic acid per one mole of nicotine, or combinations thereof, up to a concentration wherein the total amount of organic acid present is equimolar to the total amount of nicotine present in the substrate material. Various additional examples of organic acids that may be employed to produce a substrate material are described in U.S. Pat. App. Pub. No. 2015/0344456 to Dull et al., which is incorporated herein by reference in its entirety.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In some implementations, the substrate material may include other materials having a variety of inherent characteristics or properties. For example, the substrate material may include a plasticized material or regenerated cellulose in the form of rayon. As another example, viscose (commercially available as VISIL®), which is a regenerated cellulose product incorporating silica, may be suitable. Some carbon fibers may include at least 95 percent carbon or more. Similarly, natural cellulose fibers such as cotton may be suitable, and may be infused or otherwise treated with silica, carbon, or metallic particles to enhance flame-retardant properties and minimize off-gassing, particularly of any undesirable off-gassing components that would have a negative impact on flavor (and especially minimizing the likelihood of any toxic off-gassing products). Cotton may be treatable with, for example, boric acid or various organo-phosphate compounds to provide desirable flame-retardant properties by dipping, spraying or other techniques known in the art. These fibers may also be treatable (coated, infused, or both by, e.g., dipping, spraying, or vapor-deposition) with organic or metallic nanoparticles to confer the desired property of flame-retardancy without undesirable off-gassing or melting-type behavior.

In the depicted implementation, the substrate material may also include an aerosol forming material such as an aerosol precursor composition. In some implementations, the aerosol precursor composition may comprise one or more humectants such as, for example, propylene glycol, glycerin, and/or the like. In various implementations, the amount of the aerosol precursor composition that is used within the aerosol delivery device may be such that the aerosol delivery device exhibits acceptable sensory and organoleptic properties, and desirable performance characteristics. For example, in some implementations the aerosol precursor composition (such as, for example, glycerin and/or propylene glycol), may provide for the generation of a visible mainstream aerosol that in many regards resembles the appearance of tobacco smoke. For example, the amount of aerosol precursor composition incorporated into the substrate material of the smoking article may be in the range of about 4.5 grams or less, 3.5 grams or less, about 3 grams or less, about 2.5 grams or less, about 2 grams or less, about 1.5 grams or less, about 1 gram or less, or about 0.5 gram or less. It should be noted, however, that in other implementations values outside of these ranges are possible.

Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference. In some aspects, an aerosol source member may produce a visible aerosol upon the application of sufficient heat thereto (and cooling with air, if necessary), and the aerosol source member may produce an aerosol that is "smoke-like." In other aspects, the aerosol source member may produce an aerosol that is substantially non-visible but is recognized as present by other characteristics, such as flavor or texture. Thus, the nature of the produced aerosol may be variable depending upon the specific components of the aerosol delivery component. In various implementations, the aerosol source member may be chemically simple relative to the chemical nature of the smoke produced by burning tobacco.

In some implementations, the aerosol precursor composition, also referred to as a vapor precursor composition or "e-liquid," may comprise a variety of components including, by way of example, a polyhydric alcohol (e.g., glycerin, propylene glycol, or a mixture thereof), nicotine, tobacco, tobacco extract, and/or flavorants. Some possible types of aerosol precursor components and formulations are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also possible are the so-called "smoke juices" for electronic cigarettes that have been available from Johnson Creek Enterprises LLC. Still further examples of possible aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol source member is such that the aerosol generating piece provides acceptable sensory and desirable performance characteristics. For example, it is desired that sufficient amounts of aerosol forming material be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 0.5 ml or more, about 1 ml or more, about 2 ml or more, about 5 ml or more, or about 10 ml or more of the aerosol precursor composition may be included.

Referring back to FIGS. 6 and 7, as noted above the substrate portion 310 includes a plurality of susceptor bands 370, each of which includes a plurality of susceptor particles 360, wherein the susceptor particles 360 comprise the resonant receiver. In various implementations, the plurality of susceptor particles 360 may have a variety of shapes, sizes, and materials, which, in some implementations, may be combined within the same susceptor band. For example, in some implementations one or more of the plurality of susceptor particles 360 may have a substantially spherical shape, a flake-like shape, a substantially cubic shape, an irregular shape (such as, for example, a shape having one or more (e.g., multiple) sides with differing dimensions), or any combinations thereof. In various implementations, the plurality of susceptor particles 360 may comprise a ferromagnetic material including, but not limited to, cobalt, iron, nickel, zinc, manganese, and any combinations thereof. In additional implementations, the plurality of susceptor particles 360 may comprise other materials, including, for example, other porous metal materials such as aluminum or stainless steel, as well as ceramic materials such as silicon carbide, carbon materials, and any combinations of any of the materials described above. In still other implementations, the plurality of susceptor particles may comprise other conductive materials including metals such as copper, alloys of conductive materials, or other materials with one or more conductive materials imbedded therein. Although in various implementations, the size of a porous susceptor particle may vary, in some implementations one or more of the plurality of porous susceptor particles may have a diameter in the inclusive range of approximately 100 microns (0.1 mm) to approximately 2 mm, and in some implementations, one or more of the plurality of porous susceptor particles may have a diameter in the inclusive range of approximately 0.5 mm to approximately 1.5 mm.

In the depicted implementation, a change in current in the helical coil of the control body (i.e., the resonant transmitter), as directed thereto from the power source by the control component (e.g., via a driver circuit) may produce an alternating electromagnetic field that penetrates the plurality of susceptor particles 360 (i.e., the resonant receiver), thereby generating electrical eddy currents within the plurality of susceptor particles 360. The alternating electromagnetic field may be produced by directing alternating current to the helical coil. As noted above, in some implementations, the control component may include an inverter or inverter circuit configured to transform direct current provided by the power source to alternating current that is provided to the resonant transmitter.

The eddy currents flowing in the plurality of susceptor particles 360 may generate heat through the Joule effect, wherein the amount of heat produced is proportional to the square of the electrical current times the electrical resistance of the material of the plurality of susceptor particles 360. For implementations wherein the plurality of susceptor particles 360 comprises ferromagnetic materials, heat may also be generated by magnetic hysteresis losses. Several factors contribute to the temperature rise of the plurality of susceptor particles 360 including, but not limited to, proximity to the helical coil, distribution of the magnetic field, electrical resistivity of the material of the plurality of susceptor particles 360, saturation flux density, skin effects or depth, hysteresis losses, magnetic susceptibility, magnetic permeability, and dipole moment of the material.

In this regard and as noted above, both the plurality of susceptor particles 360 and the helical coil may comprise an electrically conductive material. By way of example, the helical coil and/or the plurality of susceptor particles 360 may comprise various conductive materials including metals such as copper or aluminum, alloys of conductive materials (e.g., diamagnetic, paramagnetic, or ferromagnetic materials) or other materials such as a ceramic or glass with one or more conductive materials imbedded therein. In some implementations, the plurality of susceptor particles may be coated with or otherwise include a thermally conductive passivation layer (e.g., a thin layer of glass).

In some implementations, the plurality of porous susceptor particles 360 contained in the aerosol source member may be supplemented with an additional/alternate resonant receiver. For example, in some implementations the control body of the device may include a separate resonant receiver such as, for example, one or more receiver prongs. Examples of suitable components are described in U.S. patent application Ser. No. 15/799,365, filed Oct. 31, 2017, which is incorporated herein by reference in its entirety.

Referring back to FIGS. 6 and 7, the substrate portion 310 of the some implementations may also include a cover layer 354 that is disposed around the substrate material 348. In the depicted implementation, the cover layer 354 comprises a foil sublayer 356 and a paper sublayer 358, wherein the paper sublayer 358 is disposed around the foil sublayer 356. In some implementations, the foil and paper sublayers may comprise a single laminate. In some implementations, the paper sublayer may comprise a paper or other fibrous material, such as a cellulose material. The paper sublayer material may also include at least one filler material imbedded or dispersed within the fibrous material. In various implementations, the filler material may have the form of water insoluble particles. Additionally, the filler material may incorporate inorganic components. In some implementations, the paper sublayer may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. Various types of paper materials are described in U.S. Pat. No. 5,105,838 to White et al.; 5,271,419 to Arzonico et al.; 5,220,930 to Gentry; 6,908,874 to Woodhead et al.; 6,929,013 to Ashcraft et al.; 7,195,019 to Hancock et al.; 7,276,120 to Holmes; 7,275,548 to Hancock et al.; PCT WO 01/08514 to Fournier et al.; and PCT WO 03/043450 to Hajaligol et al., which are incorporated herein by reference in their entireties. In some implementations, the paper material may comprise a commercially available material such as R. J. Reynolds Tobacco Company Grades 119, 170, 419, 453, 454, 456, 465, 466, 490, 525, 535, 557, 652, 664, 672, 676 and 680 from Schweitzer-Maudit International. In the depicted implementation, the foil sublayer 352 comprises a metal foil material, such as an aluminum foil material. In other implementations, however, the foil sublayer may comprise other materials, including, but not limited to, a copper material, a tin material, a gold material, a graphene material, a graphite material or other thermally conductive carbon-based material, and/or any combinations thereof. Although a variety of thicknesses are possible, in some implementations the cover layer may have a thickness in the inclusive range of approximately 1 mm to approximately 3 mm.

Figure 8:
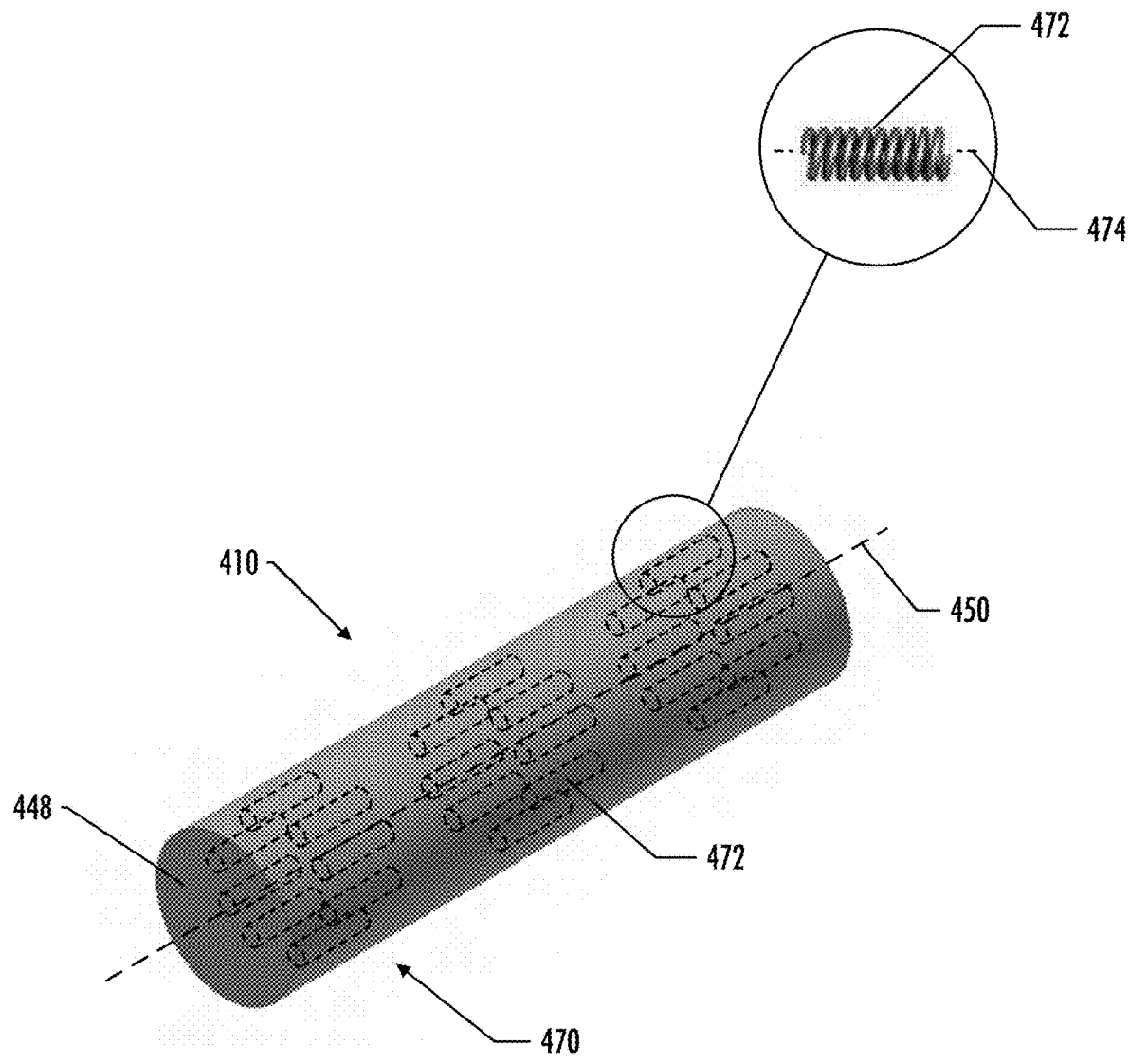
FIG. 8 illustrates a perspective schematic view of a portion of a substrate portion of an aerosol source member, according to an example implementation of the present disclosure.
Figure 9:
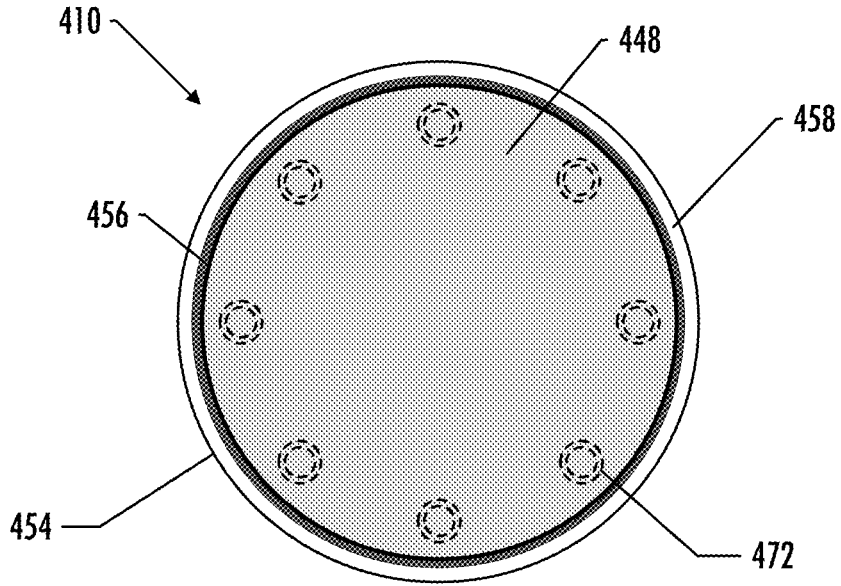
FIG. 9 illustrates a transverse cross-section schematic view of a portion of the substrate portion of the aerosol source member of FIG. 8, according to an example implementation of the present disclosure.

An alternate implementation of the present disclosure is illustrated in FIGS. 8 and 9. In particular, FIG. 8 illustrates a perspective schematic view of a portion of a substrate portion 410 of an aerosol source member, and FIG. 9 illustrates a transverse cross-section schematic view of a portion of the substrate portion 410 of the aerosol source member of FIG. 8. In various implementations, an aerosol source member having the substrate portion 410 of FIGS. 8 and 9 may be usable with various control bodies, such as, for example, the control bodies of FIGS. 1-3 and 10. In the depicted implementation, a longitudinal axis 450 is defined through the substrate portion 410, and the substrate portion 410 includes a plurality of susceptor bands 470 (see FIG. 8) that extend through at least a portion of the substrate portion 410. In various implementations, the number of susceptor bands in the substrate portion 410 may vary. For example, in some implementations there may be as few as two susceptor bands, and in other implementations there may be as many as twelve, or more, susceptor bands. Although other configurations are possible, in the depicted implementation the plurality of susceptor bands 470 are spaced along a length of the substrate portion 410. In particular, the plurality of susceptor bands 470 of the depicted implementation are substantially evenly spaced along a length of the substrate portion 410. In various implementations, a plurality of susceptor coils 472 are located within each susceptor band 470. Although other configurations are possible, in the depicted implementation the plurality of susceptor coils 472 are radially spaced around the longitudinal axis 450 of the substrate portion 410. In various implementations, the plurality of susceptor coils 472 may be located at any radial position within the substrate portion 410. For example, in some implementations the plurality of susceptor coils may be located proximate the longitudinal axis 450 of the substrate portion 410. In other implementations, the plurality of susceptor coils may be located proximate an outer surface of the substrate portion 410. In still other implementations, the plurality of susceptor coils may be located at or on the outer surface of the substrate portion 410. In various implementations, there may any number of susceptor coils within each susceptor band. For example, in some implementations there may be as few as two susceptor coils in each susceptor band. In other implementations, there may as many as twelve, or more, susceptor coils in each susceptor band. Referring to FIG. 9, in the depicted implementation there are eight susceptor coils 472 in each susceptor band 470.

Although other configurations are possible, in the depicted implementation the susceptor coils 472 are substantially evenly spaced radially around the longitudinal axis 450 of the substrate portion 410. Although other implementations are possible, each of the susceptor coils 472 of the depicted implementation defines a longitudinal axis 474, and the susceptor coils 472 are arranged such that the longitudinal axes 474 of the plurality of susceptor coils 472 are substantially parallel to the longitudinal axis 450 of the substrate portion 410.

The substrate portion 410 of the depicted implementation comprises a substrate material 448, and the plurality of susceptor coils 472 are imbedded in or dispersed within the substrate material 448. In some implementations, the substrate material may comprise an extruded tobacco structure. For example, in some implementations the extruded structure may include, or may essentially be comprised of one or more of a tobacco, a tobacco related material, glycerin, water, a binder material, and/or fillers and firming agents, such as, for example, calcium carbonate, rice flour, corn flour, etc. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass.

In some implementations, the substrate material may include an extruded material, as described in U.S. Pat. App. Pub. No. 2012/0042885 to Stone et al., which is incorporated herein by reference in its entirety. In yet another implementation, the substrate material may include an extruded structure and/or substrate formed from marumarized and/or non-marumarized tobacco. Marumarized tobacco is known, for example, from U.S. Pat. No. 5,105, 831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings. In other implementations, the extruded material may have two or more sectors, such as, for example, an extrudate with a wagon wheel-like cross section.

Additionally or alternatively, the substrate material may include an extruded structure and/or a substrate that includes or essentially is comprised of tobacco, glycerin, water, and/or binder material, and is further configured to substantially maintain its structure throughout the aerosol-generating process. That is, the substrate material may be configured to substantially maintain its shape (e.g., the substrate material does not continually deform under an applied shear stress) throughout the aerosol-generating process. Although such an example substrate material may include liquids and/or some moisture content, the substrate material may remain substantially solid throughout the aerosol-generating process and may substantially maintain structural integrity throughout the aerosol-generating process. Example tobacco and/or tobacco related materials that may be suitable for a substantially solid substrate material are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In other implementations, the substrate material may comprise a blend of flavorful and aromatic tobaccos in cut filler form. In another implementation, the substrate material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the substrate material may be formed from a wound roll of a reconstituted tobacco material. In another implementation, the substrate material may be formed from shreds, strips, and/or the like of a reconstituted tobacco material. In another implementation, the tobacco sheet may comprise a crimped sheet of reconstituted tobacco material. In some implementations, the substrate material may comprise overlapping layers (e.g., a gathered web), which may, or may not, include heat conducting constituents. Examples of substrate material that include a series of overlapping layers (e.g., gathered webs) of an initial substrate sheet formed by the fibrous filler material, aerosol forming material, and plurality of heat conducting constituents are described in U.S. patent application Ser. No. 15/905,320, filed on Feb. 26, 2018, and titled Heat Conducting Substrate For Electrically Heated Aerosol Delivery Device, which is incorporated herein by reference in its entirety.

In some implementations, the substrate material may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, the substrate material may include a plurality of microcapsules each formed into a hollow cylindrical shape. In some implementations, the substrate material may include a binder material configured to maintain the structural shape and/or integrity of the plurality of microcapsules formed into the hollow cylindrical shape.

Tobacco employed in one or more of the substrate material may include, or may be derived from, tobaccos such as flue-cured tobacco, burley tobacco, Oriental tobacco, Maryland tobacco, dark tobacco, dark-fired tobacco and Rustica tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/ 0255965 to Perfetti et al.; PCT Pub. No. WO 02/37990 to Bereman; and Bombick et al., *Fund. Appl. Toxicol.,* 39, p. 11-17 (1997); the disclosures of which are incorporated herein by reference in their entireties.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

In some implementations, flame/burn retardant materials and other additives may be included within the substrate material and may include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior. Other examples include diammonium phosphate and/or another salt configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Preferred casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. For example, some flavoring agents may be applied to, or incorporated within, the substrate material and/or those regions of the smoking article where an aerosol is generated.

In some implementations, such agents may be supplied directly to a heating cavity or region proximate to the heat source or are provided with the substrate material. Example flavoring agents may include, for example, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, may also be suitable to be employed.

Flavoring agents may also include acidic or basic characteristics (e.g., organic acids, such as levulinic acid, succinic acid, pyruvic acid, and benzoic acid). In some implementations, flavoring agents may be combinable with the elements of the substrate material if desired. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. Any of the materials, such as flavorings, casings, and the like that may be useful in combination with a tobacco material to affect sensory properties thereof, including organoleptic properties, such as described herein, may be combined with the substrate material. Organic acids particularly may be able to be incorporated into the substrate material to affect the flavor, sensation, or organoleptic properties of medicaments, such as nicotine, that may be able to be combined with the substrate material. For example, organic acids, such as levulinic acid, lactic acid, and pyruvic acid, may be included in the substrate material with nicotine in amounts up to being equimolar (based on total organic acid content) with the nicotine. Any combination of organic acids may be suitable. For example, in some implementations, the substrate material may include approximately 0.1 to about 0.5 moles of levulinic acid per one mole of nicotine, approximately 0.1 to about 0.5 moles of pyruvic acid per one mole of nicotine, approximately 0.1 to about 0.5 moles of lactic acid per one mole of nicotine, or combinations thereof, up to a concentration wherein the total amount of organic acid present is equimolar to the total amount of nicotine present in the substrate material. Various additional examples of organic acids that may be employed to produce a substrate material are described in U.S. Pat. App. Pub. No. 2015/0344456 to Dull et al., which is incorporated herein by reference in its entirety.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In some implementations, the substrate material may include other materials having a variety of inherent characteristics or properties. For example, the substrate material may include a plasticized material or regenerated cellulose in the form of rayon. As another example, viscose (commercially available as VISIL®), which is a regenerated cellulose product incorporating silica, may be suitable. Some carbon fibers may include at least 95 percent carbon or more.

Similarly, natural cellulose fibers such as cotton may be suitable, and may be infused or otherwise treated with silica, carbon, or metallic particles to enhance flame-retardant properties and minimize off-gassing, particularly of any undesirable off-gassing components that would have a nega-tive impact on flavor (and especially minimizing the likeli-hood of any toxic off-gassing products). Cotton may be treatable with, for example, boric acid or various organo-phosphate compounds to provide desirable flame-retardant properties by dipping, spraying or other techniques known in the art. These fibers may also be treatable (coated, infused, or both by, e.g., dipping, spraying, or vapor-deposition) with organic or metallic nanoparticles to confer the desired prop-erty of flame-retardancy without undesirable off-gassing or melting-type behavior.

In the depicted implementation, the substrate material may also include an aerosol forming material such as an aerosol precursor composition. In some implementations, the aerosol precursor composition may comprise one or more humectants such as, for example, propylene glycol, glycerin, and/or the like. In various implementations, the amount of the aerosol precursor composition that is used within the aerosol delivery device may be such that the aerosol delivery device exhibits acceptable sensory and organoleptic properties, and desirable performance charac-teristics. For example, in some implementations the aerosol precursor composition (such as, for example, glycerin and/or propylene glycol), may provide for the generation of a visible mainstream aerosol that in many regards resembles the appearance of tobacco smoke. For example, the amount of aerosol precursor composition incorporated into the sub-strate material of the smoking article may be in the range of about 4.5 grams or less, 3.5 grams or less, about 3 grams or less, about 2.5 grams or less, about 2 grams or less, about 1.5 grams or less, about 1 gram or less, or about 0.5 gram or less. It should be noted, however, that in other implementations values outside of these ranges are possible.

Representative types of further aerosol precursor compo-sitions are set forth in U.S. Pat. No. 4,793,365 to Sensa-baugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Mono-graph (1988); the disclosures of which are incorporated herein by reference. In some aspects, an aerosol source member may produce a visible aerosol upon the application of sufficient heat thereto (and cooling with air, if necessary), and the aerosol source member may produce an aerosol that is "smoke-like." In other aspects, the aerosol source member may produce an aerosol that is substantially non-visible but is recognized as present by other characteristics, such as flavor or texture. Thus, the nature of the produced aerosol may be variable depending upon the specific components of the aerosol delivery component. In various implementations, the aerosol source member may be chemically simple rela-tive to the chemical nature of the smoke produced by burning tobacco.

In some implementations, the aerosol precursor compo-sition, also referred to as a vapor precursor composition or "e-liquid," may comprise a variety of components including, by way of example, a polyhydric alcohol (e.g., glycerin, propylene glycol, or a mixture thereof), nicotine, tobacco, tobacco extract, and/or flavorants. Some possible types of aerosol precursor components and formulations are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also possible are the so-called "smoke juices" for electronic cigarettes that have been available from Johnson Creek Enterprises LLC. Still further examples of possible aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FAC-TORY, MECH SAUCE, CASEY JONES MAINLINE RESERVE, MITTEN VAPORS, DR. CRIMMY'S V-LIQ-UID, SMILEY E LIQUID, BEANTOWN VAPOR, CUTT-WOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol source member is such that the aerosol generating piece provides acceptable sensory and desirable performance characteristics. For example, it is desired that sufficient amounts of aerosol forming material be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 0.5 ml or more, about 1 ml or more, about 2 ml or more, about 5 ml or more, or about 10 ml or more of the aerosol precursor composition may be included.

Referring back to FIGS. 8 and 9, the substrate portion 410 includes a plurality of susceptor bands 470, each of which includes a plurality of susceptor coils 472, wherein the susceptor coils 472 comprise the resonant receiver. In vari-ous implementations, the plurality of susceptor coils 472 may have a variety of coil shapes, sizes, and materials, which, in some implementations, may be combined within the same susceptor band. For example, in some implemen-tations the plurality of susceptor coils 472 may comprise a metal material, such as a stainless steel material (e.g., a low grade stainless steel), an aluminum material, or an aluminum foil material. In other examples, the plurality of susceptor coils 472 may comprise a ferromagnetic material including, but not limited to, cobalt, iron, nickel, zinc, manganese, and any combinations thereof. In additional implementations, the plurality of susceptor coils 472 may comprise other materials, including, for example, ceramic materials such as silicon carbide, carbon materials, and any combinations of any of the materials described above. In still other imple-mentations, the plurality of susceptor coils may comprise other conductive materials including metals such as copper, alloys of conductive materials, or other materials with one or more conductive materials imbedded therein. Although the dimensions of the susceptor coils may vary, in some imple-mentations the diameter of the susceptor coils may be in the inclusive range of approximately 8.5 mm to approximately 10 mm. Various susceptor coil lengths are possible.

In the depicted implementation, a change in current in the helical coil of the control body (i.e., the resonant transmit-ter), as directed thereto from the power source by the control component (e.g., via a driver circuit) produces localized magnetic flux and hysteresis effects in the plurality of susceptor coils 472 (i.e., the resonant receiver), which then provides localized heating proximate the plurality of susceptor coils 472. As noted above, in some implementations, the control component may include an inverter or inverter circuit configured to transform direct current provided by the power source to alternating current that is provided to the resonant transmitter. For this topology, a three circuit configuration may be used, wherein one circuit comprises a half bridge rectifier, another circuit comprises a full bridge rectifier, and the third circuit comprises a transformer that can convert a direct current signal to an alternating current signal.

In various implementations, both the plurality of susceptor coils 472 and the transmitter helical coil may comprise an electrically conductive material. By way of example, the helical coil and/or the plurality of susceptor coils 472 may comprise various conductive materials including metals such as copper or aluminum, alloys of conductive materials (e.g., diamagnetic, paramagnetic, or ferromagnetic materials) or other materials such as a ceramic or glass with one or more conductive materials imbedded therein. In some implementations, the plurality of susceptor particles may be coated with or otherwise include a thermally conductive passivation layer (e.g., a thin layer of glass).

In some implementations, the plurality of porous susceptor coils 472 contained in the aerosol source member may be supplemented with an additional/alternate resonant receiver. For example, in some implementations the control body of the device may include a separate resonant receiver such as, for example, one or more receiver prongs. Examples of suitable components are described in U.S. patent application Ser. No. 15/799,365, filed Oct. 31, 2017, which is incorporated herein by reference in its entirety.

Referring to FIG. 9, the substrate portion 410 of some implementations may also include a cover layer 454 that is disposed around the substrate material 448. In the depicted implementation, the cover layer 454 comprises a foil sublayer 456 and a paper sublayer 458, wherein the paper sublayer 458 is disposed around the foil sublayer 456. In some implementations, the foil and paper sublayers may comprise a single laminate. In some implementations, the paper sublayer may comprise a paper or other fibrous material, such as a cellulose material. The paper sublayer material may also include at least one filler material imbedded or dispersed within the fibrous material. In various implementations, the filler material may have the form of water insoluble particles. Additionally, the filler material may incorporate inorganic components. In some implementations, the paper sublayer may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. Various types of paper materials are described in U.S. Pat. No. 5,105,838 to White et al.; 5,271,419 to Arzonico et al.; 5,220,930 to Gentry; 6,908,874 to Woodhead et al.; 6,929,013 to Ashcraft et al.; 7,195,019 to Hancock et al.; 7,276,120 to Holmes; 7,275,548 to Hancock et al.; PCT WO 01/08514 to Fournier et al.; and PCT WO 03/043450 to Hajaligol et al., which are incorporated herein by reference in their entireties. In some implementations, the paper material may comprise a commercially available material such as R. J. Reynolds Tobacco Company Grades 119, 170, 419, 453, 454, 456, 465, 466, 490, 525, 535, 557, 652, 664, 672, 676 and 680 from Schweitzer-Maudit International. In the depicted implementation, the foil sublayer 352 comprises a metal foil material, such as an aluminum foil material. In other implementations, however, the foil sublayer may comprise other materials, including, but not limited to, a copper material, a tin material, a gold material, a graphene material, a graphite material or other thermally conductive carbon-based material, and/or any combinations thereof. Although a variety of thicknesses are possible, in some implementations the cover layer may have a thickness in the inclusive range of approximately 1 mm to approximately 3 mm.

Figure 10:
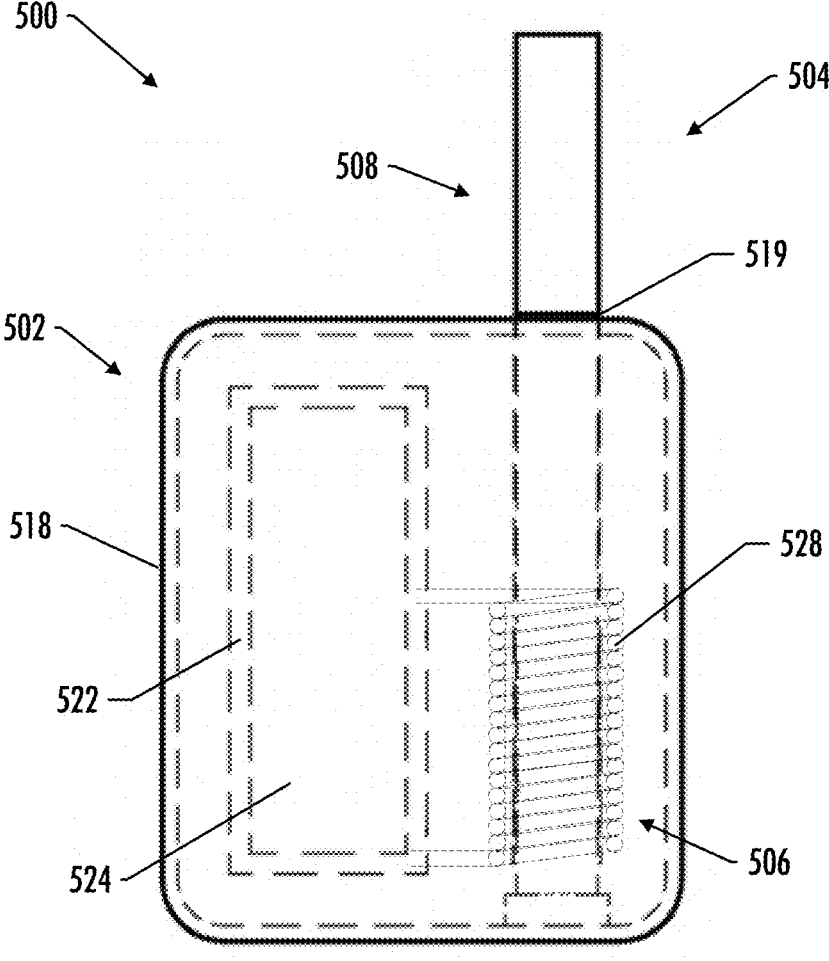
FIG. 10 illustrates a front schematic view of an aerosol delivery device, according to an example implementation of the present disclosure.

Although the control unit of the implementation of FIG. 3 is shown as being substantially cylindrical, the present disclosure is not limited to an aerosol delivery device having such a shape. For example, an alternate implementation is illustrated in FIG. 10. Similar to the implementation described with respect to FIG. 3, the implementation depicted in FIG. 10 includes an aerosol delivery device 500 comprising a control body 502 that is configured to receive an aerosol source member 504. In various implementations, the aerosol source member 504 may have a similar configuration and may include some similar components (and similar configuration and component variations) as that of the aerosol source members 104, 204 described above. As such, reference is made to the pertinent discussions of these configurations and components (and configuration and component variations). As noted above, the aerosol source member 504 may comprise a heated end 506, which is configured to be inserted into the control body 502, and a mouth end 508, upon which a user draws to create the aerosol. The control body 502 may comprise a housing 518 that includes an opening 519 defined therein, a flow sensor (not shown, e.g., a puff sensor or pressure switch), a control component 522 (e.g., a microprocessor, individually or as part of a microcontroller, a printed circuit board (PCB) that includes a microprocessor and/or microcontroller, etc.), and a power source 524 (e.g., a battery, which may be rechargeable, and/or a rechargeable supercapacitor). Examples of power sources, sensors, and various other possible electrical components are described above with respect to the example implementation of FIG. 3 above.

As with the implementation of FIG. 3, the control body 502 of the implementation depicted in FIG. 10 includes a resonant transmitter, which together with a resonant receiver form the resonant transformer. The resonant transformer of various implementations of the present disclosure may take a variety of forms, including implementations where one or both of the resonant transmitter and resonant receiver are located in the control body and/or the aerosol delivery device. In the particular implementation illustrated in FIG. 6, the resonant transmitter comprises a helical coil 528. In various implementations, the helical coil may be constructed of a conductive material. In further implementations, the helical coil may include a non-conductive insulating cover/wrap material. Although in some implementations, a resonant transmitter may surround a transmitter support member (such as a transmitter support cylinder), in the illustrated embodiment, the coil itself forms a cylinder-like structure. For example, in the illustrated implementation, the individual coils of the helical coil 528 are close to each other such that the helical coil 528 effectively creates a cylinder shape.

While not shown in the illustrated implementation, in various other implementations, the control body may include one or more positioning features located therein, which in conjunction with, or as an alternative to, an opening of the housing, may facilitate proper positioning of the aerosol source member when the aerosol source member is inserted into the control body. For example, in a further implementation, the control body of the illustrated implementation may include a positioning cylinder that extends from the opening of the housing through the helical coil such that an inner diameter of the positioning cylinder may be slightly larger than or approximately equal to an outer diameter of a corresponding aerosol source member (e.g., to create a sliding fit) so that the positioning cylinder may guide the aerosol source member into the proper position with respect to the control body.

In another aspect, the present disclosure may be directed to kits that provide a variety of components as described herein. For example, a kit may comprise a control body with one or more aerosol source members. A kit may further comprise a control body with one or more charging components. A kit may further comprise a control body with one or more batteries. A kit may further comprise a control body with one or more aerosol source members and one or more charging components and/or one or more batteries. In further implementations, a kit may comprise a plurality of aerosol source members. A kit may further comprise a plurality of aerosol source members and one or more batteries and/or one or more charging components. In the above implementations, the aerosol source members or the control bodies may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other implementations of the disclosure will come to mind to one skilled in the art to which this disclosure pertains having the benefit of the teachings presented in the foregoing descriptions and the associated drawings. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. An aerosol source member for use with an induction heated aerosol delivery device having a resonant transmitter, said aerosol source member comprising:
   a substrate portion comprising:
      a core portion;
      a surrounding portion disposed around the core portion; and a radial cover layer disposed around the surrounding portion,
   wherein the core portion includes a plurality of susceptor particles distributed therein having a first distribution density, wherein the surrounding portion includes a plurality of susceptor particles distributed therein having a second distribution density, and wherein the first distribution density is greater than the second distribution density,
   wherein the plurality of susceptor particles of the core portion are evenly distributed with respect to each other, wherein the plurality of susceptor particles of the surrounding portion are evenly distributed with respect to each other, and
   wherein the substrate portion comprises three separate radial layers: a first radial layer comprising the core portion, a second radial layer comprising the surrounding portion, and the radial cover layer.

2. The aerosol source member of claim 1, wherein the core portion and the surrounding portion comprise the same substrate material having different susceptor particle distribution densities.

3. The aerosol source member of claim 1, wherein the radial cover layer comprises a foil sublayer and a paper sublayer disposed around the foil sublayer.

4. The aerosol source member of claim 1, wherein at least one susceptor particle of the plurality of susceptor particles has a shape selected from a flake-like shape, a spherical shape, a hexagonal shape, a cubic shape, and an irregular shape.

5. The aerosol source member of claim 1, wherein at least one susceptor particle of the plurality of susceptor particles of the core portion or the surrounding portion comprises a material selected from a cobalt material, an iron material, a nickel material, a zinc material, a manganese material, a stainless steel material, a ceramic material, a silicon carbide material, a carbon material, and combinations thereof.

6. The aerosol source member of claim 1, wherein the substrate portion comprises an extruded tobacco material.

7. The aerosol source member of claim 1, wherein the substrate portion comprises a reconstituted tobacco sheet material.

8. The aerosol source member of claim 1, wherein the substrate portion comprises at least one of tobacco beads and tobacco powder.

9. The aerosol source member of claim 1, wherein the aerosol source member has a cylindrical shape.

* * * * *